United States Patent
Anderson

(10) Patent No.: US 9,782,748 B2
(45) Date of Patent: Oct. 10, 2017

(54) SYNTHESIS OF POLYMERIC IONIC LIQUIDS USING A PHOTOCHEMICAL POLYMERIZATION PROCESS

(71) Applicant: The University of Toledo, Toledo, OH (US)

(72) Inventor: Jared L. Anderson, Toledo, OH (US)

(73) Assignee: The University of Toledo, Toledo, OH (US)

( * ) Notice: Subject to any disclaimer, the term of this patent is extended or adjusted under 35 U.S.C. 154(b) by 45 days.

(21) Appl. No.: 14/404,704

(22) PCT Filed: May 30, 2013

(86) PCT No.: PCT/US2013/043275
§ 371 (c)(1),
(2) Date: Dec. 1, 2014

(87) PCT Pub. No.: WO2013/181345
PCT Pub. Date: Dec. 5, 2013

(65) Prior Publication Data
US 2015/0119231 A1    Apr. 30, 2015

Related U.S. Application Data

(63) Continuation-in-part of application No. 13/058,088, filed as application No. PCT/US2009/053319 on Aug. 10, 2009, now Pat. No. 9,249,621.
(Continued)

(51) Int. Cl.
*B01J 20/26* (2006.01)
*B01J 20/30* (2006.01)
(Continued)

(52) U.S. Cl.
CPC ....... *B01J 20/267* (2013.01); *B01J 20/28023* (2013.01); *B01J 20/3085* (2013.01); *B01J 20/3225* (2013.01); *B01J 20/3231* (2013.01); *B01J 20/3282* (2013.01); *B01J 20/3293* (2013.01); *G01N 1/405* (2013.01); *G01N 2030/009* (2013.01)

(58) Field of Classification Search
None
See application file for complete search history.

(56) References Cited

U.S. PATENT DOCUMENTS 4,409,115 A * 10/1983 Sondergeld ............... G03F 7/40
                                                        216/83
9,249,261 B2 * 2/2016 Anderson ............ C08G 65/323
(Continued)

FOREIGN PATENT DOCUMENTS

WO    WO2011/046661    * 4/2011    ............ C09K 19/34

*Primary Examiner* — Daniel Berns
(74) *Attorney, Agent, or Firm* — MacMillan, Sobanski & Todd, LLC

(57) ABSTRACT

Photo-initiated polymeric ionic liquids, methods of making and methods of using the same are disclosed. A preferred embodiment for making a photo-initiated polymeric ionic liquid (P-PIL) coated support, comprises: mixing at least one ionic liquid (IL) monomer with at least one photo-initiator; at least partially coating a support with the mixture; and exposing the coated support to UV light to form a photo-initiated polymeric ionic liquid (P-PIL) coated support.

16 Claims, 16 Drawing Sheets

Related U.S. Application Data

(60) Provisional application No. 61/653,383, filed on May 30, 2012, provisional application No. 61/087,411, filed on Aug. 8, 2008.

(51) Int. Cl.
  *B01J 20/32*  (2006.01)
  *B01J 20/28*  (2006.01)
  *G01N 1/40*  (2006.01)
  *G01N 30/00*  (2006.01)

(56) References Cited

U.S. PATENT DOCUMENTS

| | | | |
|---|---|---|---|
| 2001/0031798 A1* | 10/2001 | Wright | C08F 2/50 522/2 |
| 2006/0025598 A1* | 2/2006 | Armstrong | B01J 20/22 548/101 |
| 2011/0151139 A1* | 6/2011 | Kim | G01N 33/54353 427/558 |

* cited by examiner

Thermal-Polymerization
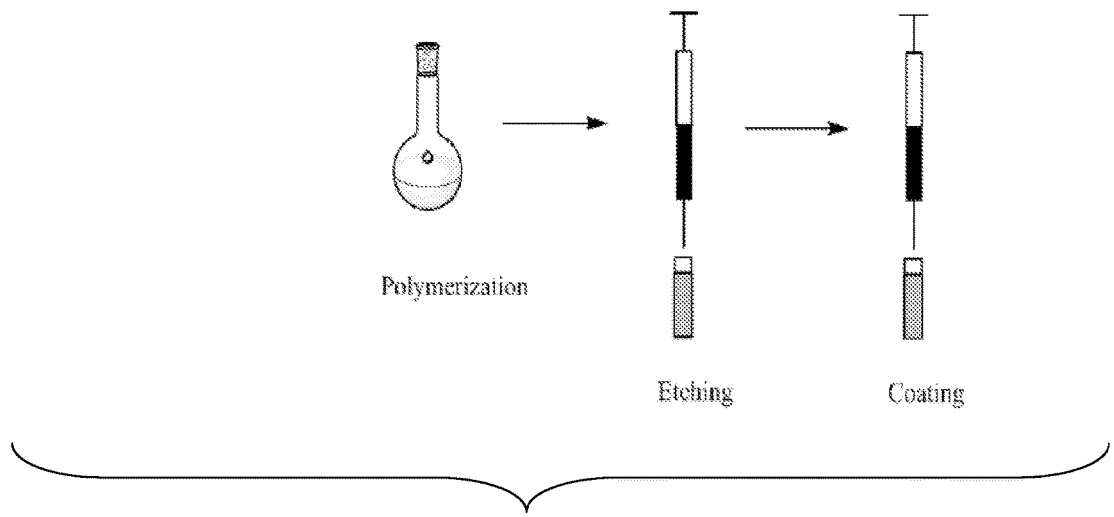
Prior Art Figure 1
Photo-Polymerization
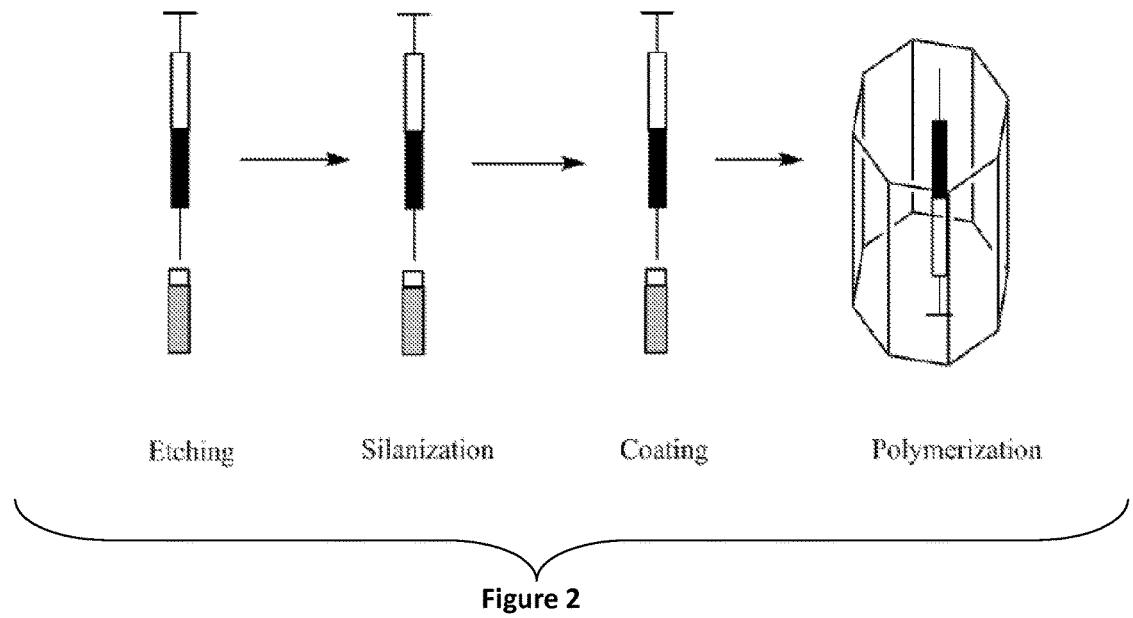
Figure 2

Fiber surface modification

STEP 1. Etching

-- Directly immersed in 5 % w/v NH4F• HF in methanol for 30 min
-- Air-dried for 30 min
-- Exposed to GC injector port at 250 °C for 1 hr

Reaction: SiO2 + 4 NH4F• HF ◊ SiF4 + 4NH4F + 2H2O

Surface comparison

Etched fiber

Etched & Derivatized fiber

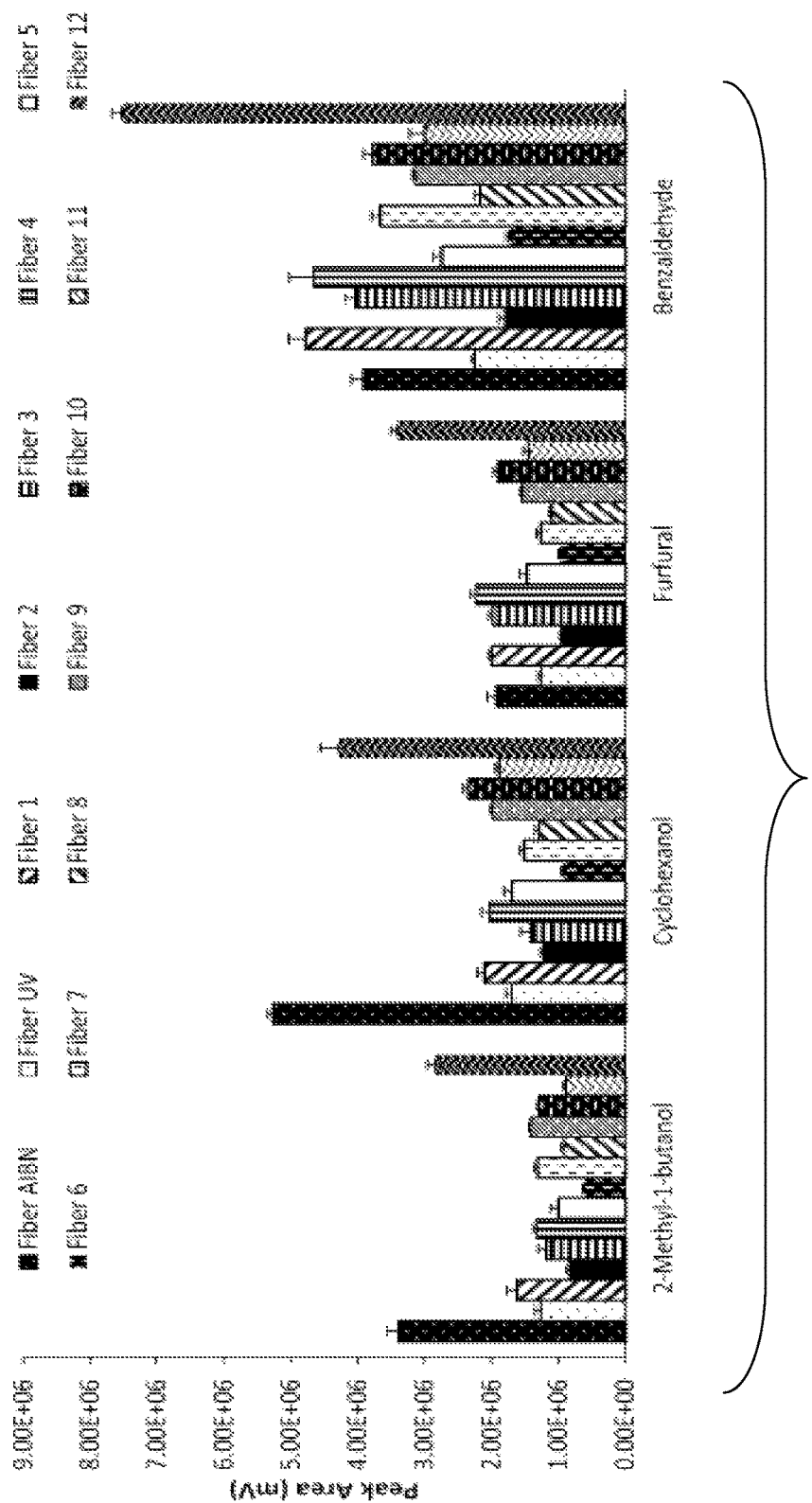
Fig.ure 14 cont.

SYNTHESIS OF POLYMERIC IONIC LIQUIDS USING A PHOTOCHEMICAL POLYMERIZATION PROCESS

CROSS-REFERENCE TO RELATED APPLICATIONS

The present application also claims the benefit of the provisional patent application Ser. No. 61/653,383 filed May 30, 2012 which is also expressly incorporated herein, by reference, in its entirety.

STATEMENT REGARDING SPONSORED RESEARCH

This invention was made with U.S. Government support under No. CHE-0748612, awarded by the National Science Foundation. The U.S. Government has certain rights in the invention.

BACKGROUND OF THE INVENTION

There is no admission that the background art disclosed in this section legally constitutes prior art.

Solid phase microextraction (SPME) is a useful solvent-free sampling technique. SPME has gained widespread acceptance and use in laboratories due to the fact that it is a solvent-less extraction technique, its mode of operation is relatively simple and easy to automate, and sampling and sample preparation are combined into one single step.

Generally, SPME uses a fiber that is coated with a stationary phase material, such as a liquid polymer, solid sorbent, or a mixture of both. Equilibrium is established between an analyte and the coating material when the fiber is exposed to a solution, which allows the technique to be applied to both headspace and direct-immersion sampling. When SPME is coupled with gas chromatography (GC), the analytes are desorbed from the fiber coating by thermal desorption in the injection port of the GC.

The development of new coating materials for SPME has flourished in the past decade as the technique continues to gain wide-spread popularity. The need for new coating materials is underscored by the fact that SPME methods must achieve high sensitivity and selectivity. The coating material must be designed to be resistant to extreme chemical conditions, such as pH, salts, organic solvents, and modifiers.

To achieve long fiber lifetimes, the coating should be thermally stable to avoid excessive losses during the high temperature desorption step, while also maintaining physical integrity of the film.

As SPME methods become more developed in sampling complicated environmental and biological matrices, structural tunability is a desirable means of modulating specific properties of the coating material while retaining others.

Solid phase microextraction (SPME) and stir bar sorptive extraction (SBSE) are two solvent-free sampling techniques in which sampling and sample preparation are combined into one single step.

SPME generally uses a fused silica fiber that is coated with an absorbent or adsorbent coating material, typically polydimethylsiloxane (PDMS), polyacrylate, or carbowax divinylbenzene. Depending on the mode of extraction (headspace or direct immersion), the analytes are sampled due to their partitioning to the coating material, typically under equilibrium conditions. The analytes are desorbed from the fiber using either thermal desorption (i.e., injection port of a gas chromatograph) or by solvent desorption (i.e., solvent chamber coupled to a high performance liquid chromatography).

SBSE operates in a similar manner to SPME but differs in the type of support and the amount of coating material employed in the extraction. In SBSE, the analytes are extracted into a thick polymer coating on a magnetic stir bar. The amount of coating material in SBSE is ~50-250 times larger than SPME, which produces a distinct sensitivity enhancement.

Polymer coating materials used in SBSE have largely focused on PDMS, although there has been a report of incorporating sol-gel technology into the PDMS coating material. The development of new coating materials for SPME has flourished in the past five years as the technique has gained wide-spread popularity.

Ionic Liquids (ILs)

Ionic liquids (ILs) are a class of compounds that can be tailor synthesized to exhibit unique solvent properties while retaining many green characteristics. Ionic liquids (IL) and their polymerized analogs constitute a class of non-molecular, ionic solvents with low melting points. Also known as liquid organic, molten, or fused salts, most ILs possess melting points lower than 100° C. Many ILs are comprised of bulky, asymmetric N-containing organic cations (e.g., imidazole, pyrrolidine, pyridine) in combination with any wide variety of anions, ranging from simple inorganic ions (e.g., halides) to more complex organic species (e.g., triflate).

ILs have negligible vapor pressures at room temperature, possess a wide range of viscosities, can be custom-synthesized to be miscible or immiscible with water and organic solvents, often have high thermal stability, and are capable of undergoing multiple solvation interactions with many types of molecules.

These interactions and properties of ILs now make molten organic salts and imidazolium and pyrrolidinium-based ILs a useful class of stationary phase materials in gas chromatography (GC). In particular, the separation selectivity and thermal stability can be altered by changes to the cation and/or anion, polymerization and immobilization of the IL, and by blending different ILs to form stationary phases with varied composition.

However, many classes of neat ILs have a strong propensity to flow off the fiber when employing moderate to high desorption temperatures (200° C. and above) and desorption times of 4 minutes or longer. Also, several complications arise from the loss of the IL during the desorption step: (1) a compromise between the desorption time and temperature must be achieved; (2) any IL present in the injection port will contaminate the liner, and the line must be constantly removed and cleaned to prevent unwanted IL-decomposition products to appear as chromatographic ghost peaks; and, (3) the support needs to be re-coated with the IL, thereby making it inconvenient while also decreasing fiber-to-fiber reproducibility.

SUMMARY OF THE INVENTION

The present invention provides an improvement over the inventor's own discovery (described in co-pending Ser. No. 13/058,088, filed Feb. 8, 2011, which is expressly incorporated herein by reference in its entirety) that an IL can be polymerized by reaction of at least one free silanol group on the surface of a fused silica support with at least one vinyl-terminated organoalkoxysilane. In one embodiment described in the Anderson '088 application, the IL comprises one or more of: vinyl-substituted IL monomers and/or cross-linkers, coated on the support with an initiator and heated to induce free radical polymerization. In a particular embodiment, the initiator comprises 2,2'-azo-bis(isobutyronitrile) (AIBN).

The present invention is based, at least in part, on an efficient method for making a coated support. In general, the method includes mixing a monomer with a photo-initiator, and, optionally, a crosslinker (to make the polymer more rigid), to form a monomer solution. The monomer solution is coated onto a support (such as fibers) and the coated support is exposed to UV radiation. A polymerization reaction occurs where a photo-initiated polymeric ionic liquid (P-PIL) is formed without the use of solvent in a very quick process. The P-PIL coated support can be conditioned using, for example, high temperatures. Thereafter, the final support can be used in any end-use reaction.

Various objects and advantages of this invention will become apparent to those skilled in the art from the following detailed description of the preferred embodiment, when read in light of the accompanying drawings.

BRIEF DESCRIPTION OF THE DRAWINGS

The patent or application file may contain at least one photograph and/or one drawing executed in color. Copies of this patent or patent application publication with color drawing(s) and/or photograph(s) will be provided by the Office upon request and payment of the necessary fee.

Prior Art FIG. 1: Schematic illustration of a polymerization route.

FIG. 2: Schematic illustration of a photo-polymerization route.

DETAILED DESCRIPTION OF THE PREFERRED EMBODIMENT(S)

Figure 3:
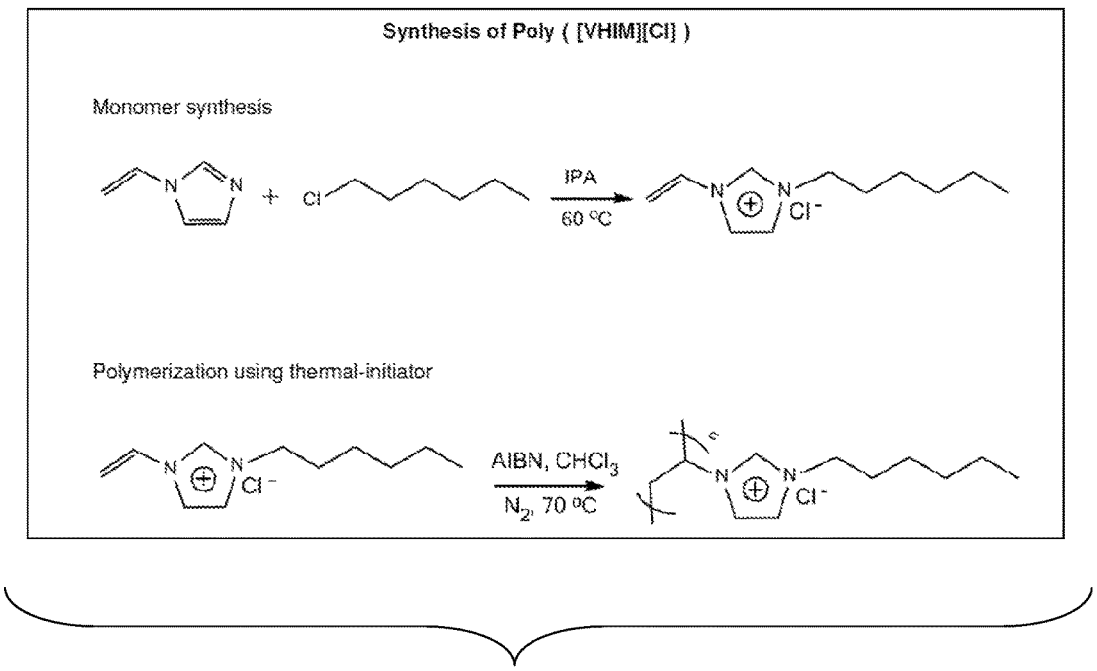
FIG. 3: Schematic illustration of synthesis of Poly ([VHIM][Cl]).
Figures 4A, 4B:
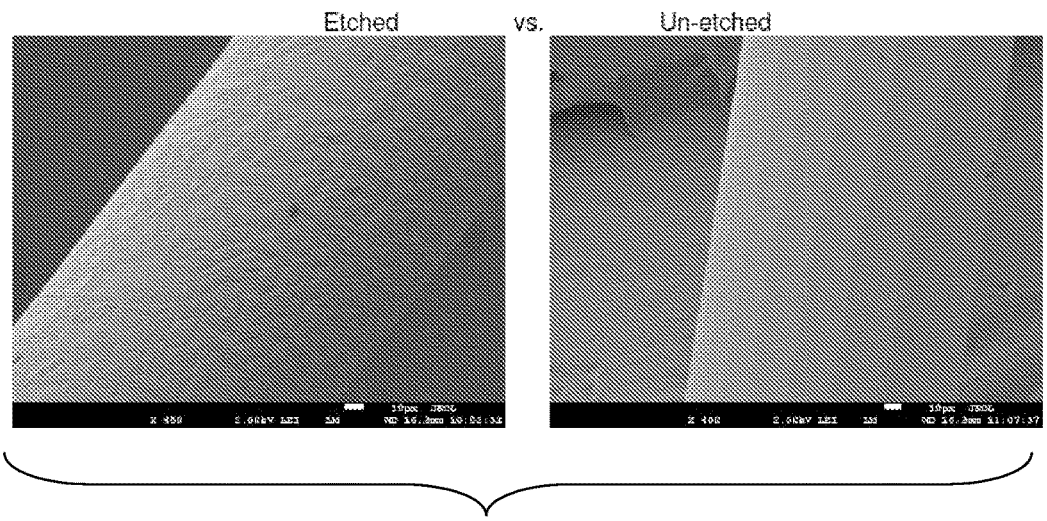
FIG. 4A: Outline of step 1 in fiber surface modification.
FIG. 4B: SEM photographs of fiber surface: etched (left), and unetched (right).
Figure 5A:
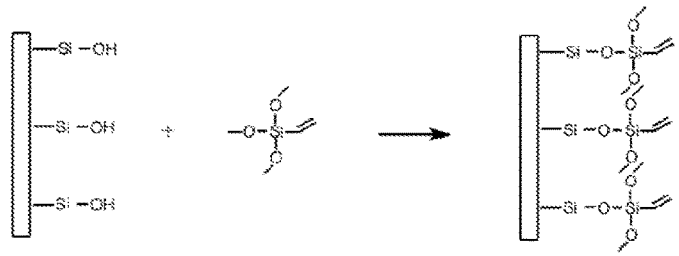
FIG. 5A: Outline of step 2—vinyl silanization.
Figure 5B:
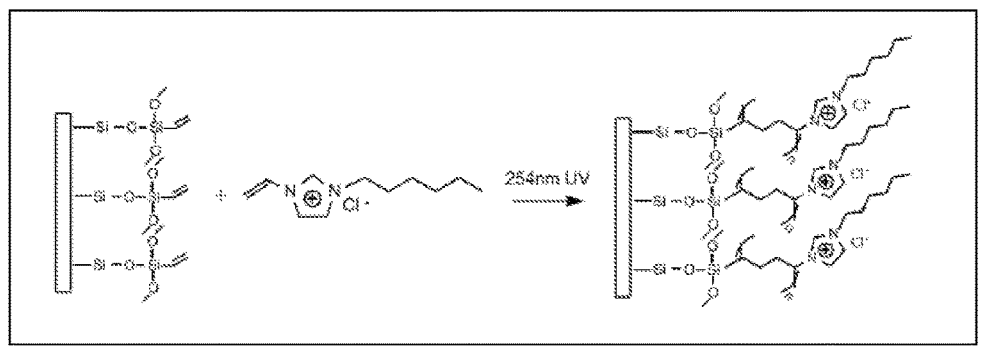
FIG. 5B: Schematic illustration of step 3—polymerization using UV light.
Figure 5C:
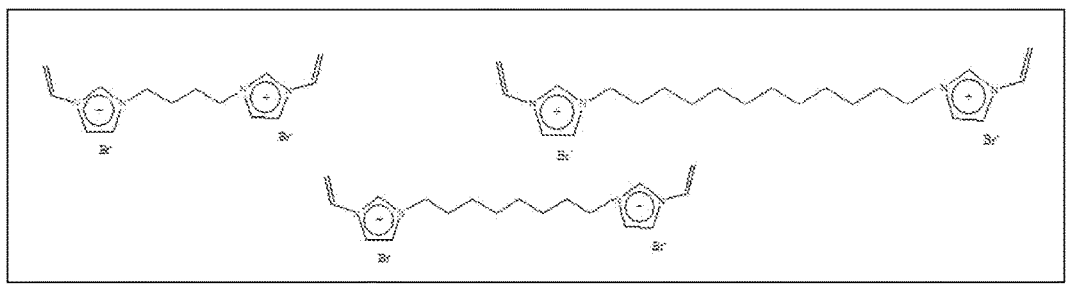
FIG. 5C: Schematic illustration of crosslinkers.

Various embodiments are described herein in the context of methods of synthesizing polymeric ionic liquids. Those of ordinary skill in the art will realize that the following detailed description of the embodiments is illustrative only and not intended to be in any way limiting. Other embodiments will readily suggest themselves to such skilled persons having the benefit of this disclosure. Reference to an "embodiment," "aspect," or "example" herein indicate that the embodiments of the invention so described may include a particular feature, structure, or characteristic, but not every embodiment necessarily includes the particular feature, structure, or characteristic. Further, repeated use of the phrase "in one embodiment" does not necessarily refer to the same embodiment, although it may.

Known methods of PIL synthesis involving AIBN polymerization utilize free-radical decomposition of AIBN to synthesis linear polymers that are coated onto fused silica fibers. However, this approach is tedious, difficult, and requires volatile solvents. The methods described herein overcome these problems by mixing a monomer and, optionally, a crosslinker with a photo-initiator, and coating the mixture as a thin film without any organic solvent. The exposure to UV light allows for the monomer to polymerize and cure on, for example, a fused silica fiber. The resulting sorbent coating exhibits sufficiently high structural integrity, can be highly crosslinked, and allows for the direct immersion sampling of various analytical matrices without the loss of coating.

The methods described herein can be practiced with a wide variety of polymer matrices in terms of the structure, composition, and chemical make-up of the corresponding cations and anions in the matrix. The products synthesized from the methods described are highly versatile in that they can be used in sampling for a variety of complex matrices. By way of non-limiting example, the P-PIL coated supports made from the methods described herein can be used to sample analyte and matrix types such as acrylamide in coffee, polychlorinated biphenyls in milk, and genotoxic impurities in active pharmaceutical ingredients.

In general, the methods described herein involve making a photo-initiated polymeric ionic liquid (P-PIL) coated support. In certain embodiment, the method includes: i) mixing at least one ionic liquid monomer (IL) with at least one photo-initiator; ii) at least partially coating a support with the mixture of step i); and, iii) exposing the coated support of step ii) to UV light to form a photo-initiated polymeric ionic liquid (P-PIL) coated support.

In certain embodiments, the method further includes adding at least one cross-linker to the mixture of step i). In certain embodiments, the method involves using dicationic IL crosslinkers and monocationic IL monomers containing halide anions. Cross-linking generally enhances the rigidity and stability of the PIL.

In certain embodiments, at least a portion of a surface of the support is functionalized prior to coating with the IL monomer mixture. The portion of the surface can be functionalized by etching prior to coating with the IL monomer mixture. For example, the portion of the surface can be functionalized by etching with a vinyl substituent prior to coating with the IL monomer mixture. Functionalization of the surface promotes copolymerization.

In certain embodiments, the method further includes heating the IL monomer mixture at a temperature of between about 35 to about 45° C. For example, the IL monomer mixture can be heated at a temperature of about 40° C.

In certain embodiments, the photo-initiator is added at about 0.5% to about 5% (m/v). For example, the photo-initiator can be added: at about 2% to about 4% (m/v); and, in certain embodiments, at about 3% (m/v). In certain embodiments, the photo-initiator is added at from about 1% to about 3% w/w of the IL monomer.

Non-limiting examples of suitable photo-initiators include: 2-hydroxy-2-methylpropiophenone (HMPP); 2,2'-azo-bis(isobutyronitrile) (AIBN); hydroxycyclohexylphenyl ketones; 4-(2-hydroxyethoxy)phenyl-(2-hydroxy-2-propyl) ketone; benzoins; benzoin alkyl ethers; benzophenones such as 2,4,6-trimethylbenzophenone and 4-methylbenzophenone; trimethylbenzoylphenylphosphine oxides such as 2,4,6-trimethylbenzoyl-diphenyl-phosphine oxide or phenylbis (2,4,6-trimethylvbenzyoyl) phosphine oxide (BAPO); azo compounds; anthraquinones and substituted anthraquinones, such as, for example, alkyl substituted or halo substituted anthraquinones; other substituted or unsubstituted polynuclear quinines; acetophenones, thioxanthones; ketals; acylphosphines; 2-hydroxy-2-methyl-1-phenyl-propan-1-one; 2-isopropyl-9H-thioxanthen-9-one; and mixtures and derivatives thereof.

In certain embodiments, the coated support of step ii) is exposed to UV light in the range of about Ultraviolet C, UVC 280-100 nm, 4.43-12.4 eV. For example, the coated support can be exposed to UV light in the range of about 250-240 nm. In another example, the coated support can be exposed to UV light in the range of about 255-253 nm.

In certain embodiments, the coated support is exposed to UV light for a time period ranging from about 0.5 to about 3 hours. For example, the coated support can be exposed to UV light for a time period ranging from about 1.5 to about 2.5 hours. In another example, the coated support can be exposed to UV light for a time period of about 2 hours. The skilled practitioner will recognize that other durations of time are possible.

In general, the P-PIL is synthesized by a polymerization reaction involving one or more functional groups attached to an aromatic ring of a cationic component. For example, the P-PIL can be synthesized using a cross-linking reaction. The degree of cross-linking can be modified to control the consistency of the formed polymer with lower degrees of cross-linking resulting in a gel-like material. Also, the degree of cross-linking can be modified to control the consistency of the formed polymer with greater degrees of cross-linking resulting in a more rigid, plastic-like coating. Thus, the degree of cross-linking can be modified to influence one or more of: the mechanism of partitioning, including adsorption versus absorption, and overall selectivity for targeted analyte molecules. Also, in certain embodiments, the P-PIL has a solid/liquid transition temperature of about 400° C. or less.

It is also to be understood that the polymerization reaction includes one or more of: cationic and anionic chain growth polymerization reactions, Ziegler-Natta catalytic polymerization, and step-reaction polymerization; use of two different monomers to form copolymers through addition and/or block copolymerization.

In certain embodiments, the IL monomer mixture is polymerized by reaction of at least one free silanol group on the surface of a fused silica support with at least one vinyl-terminated organoalkoxysilane. In another embodiment, the IL monomer mixture comprises one or more of: vinyl-substituted IL monomers, initiators and/or cross-linkers. It is to be understood that P-PIL coated support can be polymerized to form linear polymers and/or cross-linked using varying ratios of monocationic/dicationic/tricationic/multicationic crosslinking molecules.

In particular embodiments, the photo-initiated polymeric ionic liquid (P-PIL) comprises: a) at least one cationic component comprised of an ionic liquid (IL); and, b) one or more anionic components, wherein the anionic components can be the same or different.

In other particular embodiments, the P-PIL comprises a cationic photo-initiated polymeric ionic liquid (c-P-PIL) comprised of: a) at least one ionic component comprised of anionic liquid (IL): and, b) one or more mobile cationic components, wherein the cationic components can be the same or different.

In certain embodiments, the cationic component can be one or more of: monocationic components, dicationic components, tricationic components, other multicationic components, and mixtures thereof. Also, in certain embodiments, the cationic component can be an IL monomer modified through one or more of: incorporation of longer alkyl chains, aromatic components, and/or hydroxyl-functionality.

Non-limiting examples of the cationic component include at least one or more: quaternary ammonium, protonated tertiary amine, thionium, phosphonium, arsonium, carboxylate, sulfate or sulfonate groups which may be substituted or unsubstituted, saturated or unsaturated, linear, branched, cyclic or aromatic.

Also, the cationic component can be described by the general formula of $-X\ ^+RR'R''$, where X is selected from the group consisting of N, P, and As, and where each of R, R', R'' is selected from the group consisting of a proton, aliphatic group, cyclic group and aromatic group. Also, the cationic component can be described by the formula of $(-X(R)_3)^+$, wherein R is selected from the group consisting of a proton, aliphatic group (e.g., propyl, butyl), cyclic group (e.g., cyclohexane) and aromatic group (e.g., vinyl, phenyl). In certain embodiments, the R, R' and R'' are different from each other.

It is also to be understood that, in certain embodiments, the cationic component can include one or more amine functional groups within the cation. In particular embodiments, the cationic component can comprise one or more of: imidazolium-based monomers including functionalized imidazolium, pyridinium, triazolium, pyrrolidinium, ammonium. For example, the cationic component can comprises: a quaternary ammonium, a protonated tertiary amine, imidazolium (IM) or substituted IM, pyrrolidinium or substituted pyrrolidinium, or pyridinium or substituted pyridinium, thiophene, N-methyl-D-glucaminium cations and related structures.

Non-limiting specific examples of suitable cationic components include one or more of: $VHIM^+$; $VDDIM^+$, $VHDIM^+$, or $BBIM^+$. By way of non-limiting example, the P-PIL can include one or more of: poly($VHIM^+$ $NTf_2^-$); poly($VDDIM^+$ $NTf_2^-$), poly($VHDIM^+$ $NTf_2^-$), poly($BBIM^+$ $NTf_2^-$), poly($BBIM^+$ taurate$^-$), or poly($BBIM^+$ $A^-$).

In general, during the polymerization of P-PIL coated support, the anionic component is exchanged through biphasic anion metathesis with one or more of the cationic components.

It is to be understood that P-PIL coated support can include anionic components comprised or one or more of: carboxylate, sulfate or sulfonate groups which may be substituted or unsubstituted, saturated or unsaturated, linear, branched, cyclic or aromatic.

In certain embodiments, the anionic group can be comprised of an amino acid component, bis[(trifluoromethyl) sulfonyl]imide, or any anion containing i) fluorine groups and ii) primary, secondary, or tertiary amine groups. Also, in certain embodiments, the anionic group comprises a taurate component.

Non-limiting examples of anionic component include one or more of: $Cl^-$, $Br^-$, $I^-$, bis[(trifluoromethyl)sulfonyl]imide, $PF_6^-$, $BF_4^-$, $CN^-$, $SCN^-$, taurate. For example, the P-PIL coated support can be synthesized by free radical polymerization of one or more of: 1-vinyl-3-hexylimidazolium chloride, 1-vinyl-3-dodecylimidazolium bromide, and 1-vinyl-3-hexadecylimidazolium bromide.

In another broad aspect, there is provided herein devices that include a P-PIL coated support that is one or more of: a solid fused silica support, a stir bar, a fiber, a film, a membrane, a fibrous mat, a woven or non-woven material. For example, the P-PIL coated support can comprise one or more walls of fused silica capillaries. In another example, the P-PIL coated support can comprise small inner diameter fused silica supports.

In certain embodiments, the methods described herein can be performed in air at room temperature and consolidated to two primary steps: dynamic dip coating, and exposure to UV radiation. Compared to other PIL coating methods, the methods described herein require fewer steps and eliminate the need for applied heat, dispersive organic solvents, and an inert $N_2$ atmosphere. The etching of the support allows for a higher surface area and a more rigid surface morphology. Derivatizing the surface with VTMS to impart vinyl functionality to the fiber allows the copolymer matrix to be covalently bonded to the support. Immobilization of the cross-linked PIL-based sorbent coating to the silica support also hinders the sloughing off of the coating during direct immersion SPME, particularly in well agitated samples.

In certain embodiments, the methods described herein eliminate the need for organic solvents, produce a covalently linked and mechanically stable coating capable of enduring high shear forces, and exhibit lower bleed, lower backgrounds, and lower limits of detection. The resulting coatings are nonetheless stable in the presence of different organic solvents and aqueous matrices, and are thus rather versatile.

Non-limiting uses of the P-PIL coated supports and devices include a chemical separation or analysis device. For example, the P-PILs in the device can be functionalized to: 1) selectively extract one or more analytes of interest and to allow all other analytes to be removed so that one or more pre-concentrated analytes can be separated, identified and/or quantified; and/or 2) selectively extract all other molecules so that the analyte(s) of interest can be removed from other molecules thereby allowing them to be separated, identified, and/or quantified.

One example is a separation device having a support at least partially coated with one or more photo-initiated polymeric ionic liquids (P-PILs). The separation device can be one or more of: headspace extraction, direct-immersion extraction, or membrane protected SPME extraction. Also, in certain examples, the separation device can be coupled to gas chromatography (GC) in which one or more analytes are thermally desorbed in a GC injection port. In another example, the separation device can be coupled to HPLC in which a HPLC mobile phase or buffered component is used to desorb molecules from the support. In yet another example, the separation device can be coupled to capillary electrophoresis (CE) in which a running buffer from the CE is used to remove analytes from the support.

It is to be understood that the separation devices described herein are useful where one or more analytes to be separated exist as any one of forms of solids, liquids and gases, and are any one of chemical component comprising: small molecules, ions, synthetic or natural polymers, macromolecules and biomolecules.

Another example is an extraction device having at least one photo-initiated polymeric ionic liquids (P-PILs). The extraction device can be one or more of: liquid-phase microextraction and single drop microextraction devices. For example, the extraction device can include the P-PIL coated support packed in a chromatographic column. In a particular embodiment, the P-PIL coated support can be a capillary column of a gas chromatography device. In another non-limiting example, the extraction device can be a solid phase microextraction (SPME) device. In another non-limiting example, the device can be a high performance liquid chromatography column (HPLC).

It is to be understood that the P-PIL is adaptable to desorption after exposure to one or more analytes. For example, the extraction device is useful for extracting one or more of DNA, RNA, protein, nucleic acids, peptides, amino acids, cellular extracts and portions thereof, comprising at least one P-PIL coated support.

Other non-limiting examples of devices include: a selective $CO_2$ absorbance device, and a sequestration of $CO_2$ device. It is to be understood that the method for capturing $CO_2$ can include exposing an environment containing $CO_2$ to at least one P-PIL coated support. Also, in certain embodiments, the P-PIL coated support can be heated to temperatures around 70-110° C. to release $CO_2$ from the P-PIL support. Also, it is to be understood that in a carbon sequestration method, at least one of a reactant gas mixture including $CO_2$ can be brought into contact with P-PIL carbon sequestration catalyst at a temperature wherein a solid carbon deposit is formed at the surface of the P-PIL carbon sequestration catalyst. Also, in certain embodiments, the method can further include recapturing sequestered $CO_2$ and reusing the P-PIL carbon sequestration catalyst.

Yet another example is a method of separating at least one chemical from a mixture of chemicals comprising: providing a mixture containing the at least one chemical; exposing the mixture to at least one solid support including at least one P-PIL adsorbed, absorbed or immobilized thereon; and, retaining at least a portion of the at least one chemical on the solid support for a period of time. In certain embodiments, the solid support is a column, and the method further comprises passing the mixture through the column such that elution of the at least one chemical is prevented or delayed.

The skilled practitioner will appreciate that the versatile copolymerization approach described herein can be easily expanded to IL monomers/cross-linkers with varied chemical structures and cation/anion combinations.

Examples of Support

In certain embodiments, the extraction additives or phase modifiers comprise one or more of: micelles, monomer surfactants, cyclodextrins, nanoparticles, synthetic macrocycles, or other polymer aggregates.

In certain embodiments, the support comprises one or more of: fibers at least partially coated with at least one P-PIL; stir bar supports; walls of fused silica capillaries; small inner diameter fused silica supports.

In another broad aspect, there is provided herein a stationary phase microextraction material (SPME) for solid phase microextraction comprising one or more P-PILs. In certain embodiments, the solid phase microextraction material can further include one or more of: a support at least partially coated with the polymeric ionic liquid; fibers at least partially coated with the polymeric ionic liquid; fibers that comprise small inner diameter fused silica fibers.

Examples of P-PILs

The photo-initiated polymeric ionic liquids (P-PILs) are generally comprised of: i) a cationic component comprised of an ionic liquid (IL) that is polymerized, and ii) one or more anionic components, wherein the anionic components can be the same or different.

Cationic Components

In certain embodiments, the cationic component comprises at least one or more: quaternary ammonium, protonated tertiary amine, thionium, phosphonium, arsonium, carboxylate, sulfate or sulfonate groups which may be substituted or unsubstituted, saturated or unsaturated, linear, branched, cyclic or aromatic.

In certain embodiments, the cationic component is described by the general formula of —X$^+$RR'R", where X is N, P, or As, and where each of R, R', R" is selected from the group consisting of a proton, aliphatic group, cyclic group, and aromatic group.

In certain embodiments, the cationic component is described by the formula of (—X(R)$_3$)$^+$, wherein R is a proton, aliphatic group (e.g., propyl, butyl), cyclic group (e.g., cyclohexane), or aromatic group (e.g., vinyl, phenyl). For example, in certain embodiments, the R, R', and R" are different from each other.

Non-limiting examples include where the cation comprises one or more of: imidazolium-based monomers including functionalized imidazolium, pyridinium, triazolium, pyrrolidinium, ammonium. Other non-limiting examples include where the anion comprises one or more of: Cl$^-$, Br$^-$, I$^-$, bis[(trifluoromethyl)sulfonyl]imide, PF$_6^-$, BF$_4^-$, CN$^-$, SCN$^-$, taurate, and/or other amino acid groups.

In certain embodiments, the P-PIL is substantially free of residual halides following anion metathesis.

In certain embodiments, the P-PIL comprises one or more of: 1-vinyl-3-hexylimidazolium chloride; 1-vinyl-3dodecylimidazolium bromide, and 1-vinyl-3-hexadecylimidazolium bromide.

In certain embodiments, the cationic component comprises: a quaternary ammonium, a protonated tertiary amine, imidazolium (IM) or substituted IM, pyrrolidinium or substituted pyrrolidinium, or pyridinium or substituted pyridinium.

In certain embodiments, the cationic component includes one or more amine functional groups within the cation.

In certain embodiments, the P-PIL is polymerized to form linear polymers and/or cross-linked using varying ratios of monocationic/dicationic/tricationic/multicationic crosslinking molecules.

In certain embodiments, the cationic component comprises one or more of: monocationic components, dicationic components, tricationic components, other multicationic components, and mixtures thereof.

In certain embodiments, the cationic component comprises an IL monomer modified through one or more of: incorporation of longer alkyl chains, aromatic components, and/or hydroxyl-functionality. Non-limiting examples include wherein the cationic component comprises one or more of: VHIM$^+$; VDDIM$^+$, VHDIM$^+$, and BBIM$^+$.

In addition, other non-limiting examples include where the P-PIL includes one or more of: poly(VHIM$^+$ NTf$_2^-$); poly(VDDIM$^+$ NTf$_2^-$), poly(VHDIM$^+$ NTf$_2^-$), poly(BBIM$^+$ NTf$_2^-$), poly(BBIM$^+$ taurate$^-$), poly(BBIM$^+$ A$^-$).

Anionic Components

In certain embodiments, the anionic component comprises one or more of: carboxylate, sulfate or sulfonate groups which may be substituted or unsubstituted, saturated or unsaturated, linear, branched, cyclic or aromatic.

In certain embodiments, the anionic component comprises an amino acid component, bis[(trifluoromethyl)sulfonyl]imide, or any anion containing i) fluorine groups and ii) primary, secondary, or tertiary amine groups. In a specific example, the anionic group comprises a taurate component.

In certain embodiments, the structural design of the P-PIL is selected in order to achieve high thermal stability.

In certain embodiments, the P-PILs have a solid/liquid transition temperature of about 400° C. or less.

In certain embodiments, the P-PIL comprises one or more of non-molecular ionic solvents, the solvent being comprised of at least one asymmetric cation paired with at least one anion.

In certain embodiments, the anionic component is exchanged through biphasic anion metathesis with one or more of the cationic components.

Diionic Salts

A "diionic salt" or "DIS" is a salt formed between a dication and a dianion or two anions or between a dianion as described herein and a dication or two cations. This term is not meant to embrace a single species that has a +2 or −2 charge such as Mg$^{+2}$ or SO$_4^{-2}$. Rather, it contemplates a single molecule with two discreet mono-ionic groups, usually separated by a bridging group. The two ionic species are of the same charge. They may be different types of groups or the diionic liquid salts may be "geminal" which means both ionic groups are not only the same charge, but also the same structure. The counterions need not be identical either. In one embodiment, either the diion or the salt forming species is chiral, having at least one stereogenic center. In such instances, the diionic liquid salts may be racemic (or in the case of diastereomers, each pair of enantiomers is present in equal amounts) or they may be optically enhanced. "Optically enhanced" in the case of enantiomers means that one enantiomer is present in an amount which is greater than the other. In the case of diastereomers, at least one pair of enantiomers is present in a ratio of other than 1:1. The diionic liquid salts may be "substantially optically pure" in which one enantiomer or, if more than one stereogenic center is present, at least one of the pairs of enantiomers, is present in an amount of at least about 90% relative to the other enantiomer. The diionic liquid salts of the invention may also be optically pure, i.e., at least about 98% of one enantiomer relative to the other.

The term diionic salt is used to describe a salt molecule, although, it may be used synonymously with "diionic liquid" ("DIL") and "diionic liquid salt" (DILS"). A "diionic liquid" or "DIL" is a liquid comprised of diionic salts. Thus, sufficient DS molecules are present such that they exist in liquid form at the temperatures indicated herein. This presumes that a single DS molecule is not a liquid. A DL is either a dicationic ionic liquid or a dianionic ionic liquid (a liquid comprising either dicationic salts or dianionic salts as described herein). A "dicationic ionic liquid" (used synonymously with "liquid salts of a dication") is a liquid comprised of molecules which are salts of dicationic species. The salt forming counter-anions may be mono-ionic such as, for example only, Br—, or dianionic, such as, again for example only, succinic acid. Any dicationic ionic liquid which is stable and has a solid/liquid transformation temperature of 400° C. or less is contemplated. The same is true for "dianionic ionic liquids" also known as "liquid salts of a dianion," except the charges are reversed. Dicationic liquids and dianionic liquids can also be referred to herein as diionic liquid salts ("DILS" or "DCLS" and "DALS" depending upon charge).

In certain preferred embodiments, a dicationic ionic liquid and/or dianionic ionic liquid will not substantially decompose or volatilize (or remain substantially non-volatile) as measured by being immobilized as a thin film in a fused silica capillary or on a silica solid support as described herein, at a temperature of 200° C. or less. "Substantially" in this context means less than about 10% by weight will decompose or volatilize at 200° C. inside a capillary over the course of about one hour. Moreover, the dicationic ionic liquid will preferably have either a solid/liquid transformation temperature at about 100° C. or less or a liquid range (the range of temperatures over which it is in a liquid form without burning or decomposing) of at least 200° C.

In another embodiment, these dicationic ionic liquids will have both a solid/liquid transformation temperature at about 100° C. or less and a liquid range of at least 200° C.

In another embodiment, a dicationic ionic liquid will not substantially volatilize or decompose, at a temperature of less than about 300° C. "Substantially" in this context means that less than about 10% by weight will decompose or volatilize at 300° C. inside a capillary over the course of about one hour. Moreover, the dicationic ionic liquids will preferably have either a solid/liquid transformation temperature at 25° C. or less. In another embodiment, the dicationic ionic liquids will also have a liquid range of at least 200° C. In another embodiment, the liquid range will be 300° C. or above.

In other embodiments in accordance with the present invention, the diionic liquids, either dicationic ionic liquids or dianionic ionic liquids will be stable, that is not substantially volatilized or decomposed, as discussed herein, at a temperature of less than about 300° C. and will have a solid/liquid transformation temperature at about 25° C. or less. In one preferred embodiment, the diionic liquids will have a liquid range of at least 200° C., and even more preferably at least 300° C. Any diionic compound which can form a stable liquid salt that meets the broadest parameters is contemplated.

In another embodiment, the present invention provides a stable diionic liquid comprising at least one liquid salt of dianionic molecule or dicationic molecule of the structure of formula I or II: C-A-B-A' (I) or C'-A-B-A'-C" (II) wherein A and A' are either both anions or both cations, or are both groups which overall have an anionic or cationic charge and which may be the same or different, so long as they both have the same charge (positive or negative); B is a bridging group (also referred to as a chain or bridging moiety) that may be substituted or unsubstituted, saturated or unsaturated, aliphatic, including straight or branched chains, cyclic or aromatic, and which may contain, in addition to carbon atoms and hydrogen, N, O, S and Si atoms; and C, C' and C" are counter ions having a charge which is opposite that of A and A'. C' and C" are ether both mono-anionic or monocationic or groups which have a single anionic or cationic charge and may be the same or different so long as they both have the same charge (positive or negative) and C is ether dianionic or dicationic or contains two groups which each have a single anionic or cationic charge.

In another embodiment, A and A' are cationic and are, without limitation, substituted or unsubstituted, saturated or unsaturated, aliphatic including straight or branched chain, cyclic or aromatic, quaternary ammonium, protonated tertiary amine, phosphonium or arsonium groups. When A and A' are cationic, C' and C" are anionic counterions which, without limitation, include halogens, mono-carboxylates, mono-sulfonates, mono-sulphates, $NTf_2^-$, $BF_4^-$, triflates or $PF_6^-$, and C is a dianionic molecule having two anionic groups each selected from, without limitation, carboxylate, sulfate or sulfonate groups. In another embodiment, A and A' are anionic and are, without limitation, substituted or unsubstituted, saturated or unsaturated, aliphatic including straight or branched chain, cyclic or aromatic, carboxylates, sulfonates, and sulphates. When A and A' anionic, C' and C" are cationic counterions which, without limitation, include quaternary ammonium, protonated tertiary amine, phosphonium or arsonium groups. C is a dicationic molecule which can be, without limitation, a compound having two cationic groups each selected from quaternary ammonium, protonated tertiary amine, phosphonium or arsonium groups. In another embodiment, these dianionic ionic liquids will have both a temperature of solid/liquid transformation of about 100° C. or less and a liquid range of at least 200° C. In one preferred embodiment, these liquid salts of formula I or II have a solid/liquid transition temperature of from about 100° C. or less and/or a liquid range of 200° C. or more and/or are substantially non-volatile and non-decomposable at temperatures below 200° C.

In certain embodiments, the structural considerations for diionic liquids are the same whether they are dianionic ionic liquids or dicationic ionic liquids. First, the diionic liquids will include a diionic species, either a dianionic or a dicationic molecule. The ionic species are normally separated by a chain or bridging moiety or group as discussed herein. Any anion or cation which can provide a dianionic ionic liquid or dicationic ionic liquid is contemplated. These include those that are identified above as A and A'. Possible cations include, without limitation, quaternary ammonium $(-N(R)_4)^+$, protonated tertiary amines $(-N(R)_3H)^+$, phosphonium and arsonium groups. These groups can be aliphatic, cyclic, or aromatic.

Anions may include, for example, carboxylates, sulphonates, or sulphonates. Examples of a dicarboxylic acid dianion include, without limitation, succinic acid, nonanedioic acid, and dodecanedioic acid. Other non-limiting examples of diionic species (dianions an dications including a generic bridging group) include:

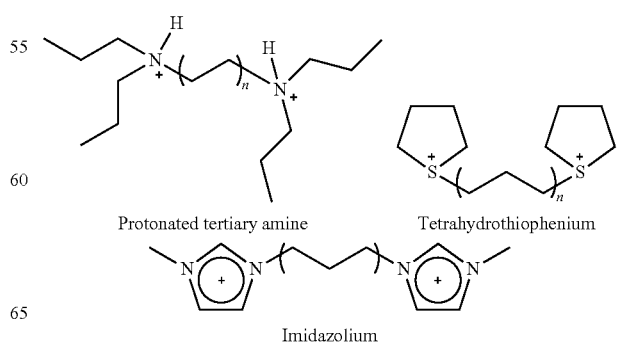

Protonated tertiary amine    Tetrahydrothiophenium

Imidazolium

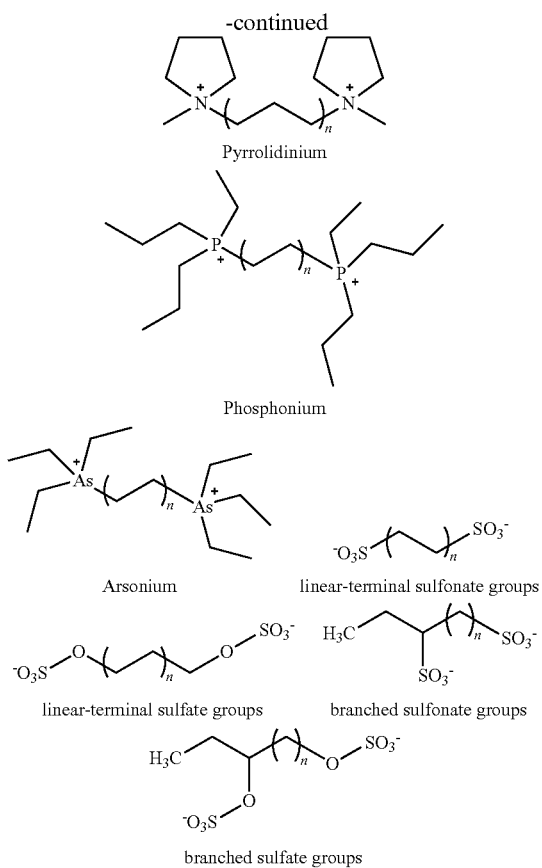

Pyrrolidinium

Phosphonium

Arsonium linear-terminal sulfonate groups linear-terminal sulfate groups branched sulfonate groups branched sulfate groups The value of n is discussed in connection with the length of the bridging group. In addition, hybrid dianions and dications are contemplated. Thus, for illustration only, a dication can be composed of a quaternary ammonium group and an arsonium group and a dianion can be composed of a carboxylate group and a sulphonate. The counter ions may also be different from each other.

The bridging group or chain interposed between the two ionic species can be any length or any composition which affords a diionic liquid of suitable properties. These include the groups identified as B above. There are certain factors that should be considered in selecting such a chain or bridging moiety. First, the larger the diionic molecule in general, the greater the chance that the melting point or temperature of solid/liquid transformation will be elevated. This may be less of a concern where the liquid range need not be extensive and the temperature of solid/liquid transformation need not be terribly low. If, however, one desires a liquid range of about 200° C. or more and/or a solid/liquid transformation temperature at 100° C. or less, the size of the overall molecule can become a larger and larger factor. Second, the chain should have some flexibility. An excessive degree of unsaturated groups, the use of very rigid and/or stericly bulky groups can adversely impact the ability of the resulting materials to act as solvents and reduce their overall and utility. Thus, multiple fused ring structures, such as those found in, for example, cholesterol, and polyunsaturated aliphatic groups with extensive unsaturation should generally be avoided.

In general, the length of the bridging group can range from a length equivalent to that of a saturated aliphatic carbon chain of between about 2 and about 40 carbon atoms (e.g., $n=C_2$-$C_{40}$ when bridging group is composed of carbon). More preferably, the length should be approximately that resulting from a saturated aliphatic carbon chain of about 3 to about 30 carbon atoms in length.

The chain or bridging group may be aliphatic, cyclic, or aromatic, or a mixture thereof. It may contain saturated or unsaturated carbon atoms or a mixture of same with, for example, alkoxy groups (ethoxy, propoxy, isopropoxy, butoxy, and the like). It may also include or be made completely from alkoxy groups, glycerides, glycerols, and glycols. The chain may contain hetero-atoms such as O, N, S, or Si and derivatives such as siloxanes, non-protonated tertiary amines and the like. The chain may be made from one or more cyclic or aromatic groups such as a cyclohexane, an immidazole, a benzene, a diphenol, a toluene, or a xylene group or from more complex ring-containing groups such as a bisphenol or a benzidine. These are merely representative and are not meant to be limiting. Generally, however, the bridging group will not contain an ionically charged species, other than the dianions or dications.

The diionic liquids are generally salts, although they may exist as ions (+1, −1, +2, −2) in certain circumstances. Thus, in most instances, each ion should have a counterion, one for each anion or cation. Charge should be preserved. In the case of a dianionic ionic liquid, two cations (including those identified as C' or C") (or one dication) (including those identified as C) are required and in the case of a dicationic ionic liquid, two anions (including those identified as C' or C") (or one dianion) (including those identified as C) are required. The choice of anion can have an effect of the properties of the resulting compound and its utility as a solvent. And, while anions and cations will be described in the context of a single species used, it is possible to use a mixture of cations to form salts with a dianionic species to form a dianionic ionic liquid. The reverse is true for dications. For clarity sake, the salt-forming ions will be referred to as counterions herein.

Cationic counterions can include any of the dicationic compounds previously identified for use in the production of dicationic ionic liquids. In addition, monoionic counterparts of these may be used. Thus, for example, quaternary ammonium, protonated tertiary amines, phosphonium, and arsonium groups are useful as cationic counterions for dianionic molecules to form dianionic ionic liquids.

Similarly, anionic counterions can be selected from any of the dianionic molecules discussed herein useful in the creation of dianionic ionic liquids. These include dicarboxylates, disulphonates, and disulphates. The corresponding monoionic compounds may also be used including carboxylates, sulphonates, sulphates and phosphonates. Halogens may be used as can triflate, $NTf_2^-$, $PF_6^-$, $BF_4^-$ and the like. The counterions should be selected such that the diionic liquids have good thermal and/or chemical stability and have a solid/liquid transformation temperature and/or a liquid range as described herein.

The ionic groups can be substituted or unsubstituted. They may be substituted with halogens, with alkoxy groups, with aliphatic, aromatic, or cyclic groups, with nitrogen-containing species, silicon-containing species, with oxygen-containing species, and with sulphur-containing species. The degree of substitution and the selection of substituents can influence the properties of the resulting material as previously described in discussing the nature of the bridge or chain. Thus, in certain embodiments, care should be taken to ensure that excessive steric hindrance and excessive molecular weight are avoided, that resulting materials does not lose its overall flexibility and that nothing will interfere with the ionic nature of the two ionic species.

The diionic liquids can be used in pure or in substantially pure form as carriers or as solvents. "Substantially" in this context means no more than about 10% of undesirable impurities. Such impurities can be either other undesired diionic salts, reaction by-products, contaminants or the like as the context suggests. In an intended mixture of two or more DILS, neither would be considered an impurity. Because they are non-volatile and stable, they can be recovered and recycled and pose few of the disadvantages of volatile organic solvents. Because of their stability over a wide liquid range, in some instances over 400° C., they can be used in chemical syntheses that require both heating and cooling. Indeed, these solvents may accommodate all of the multiple reaction steps of certain chemical syntheses. These diionic liquids may be used in solvent systems with cosolvents and gradient solvents and these solvents can include, without limitation, chiral ionic liquids, chiral non-ionic liquids, volatile organic solvents, non-volatile organic solvents, inorganic solvents, water, oils, etc. It is also possible to prepare solutions, suspensions, emulsions, colloids, gels and dispersions using the diionic liquids.

In addition to discrete diionic salts and diionic liquid salts, it is also possible to produce polymers of these materials. Polymers may include the diionic salts within the backbone or as pendant groups and they may be cross-linked or non-cross-linked.

In addition to being useful as solvents and reaction solvents, the dianionic liquids can be used to perform separations as, for example, the stationary phase for gas-liquid chromatography. Dicationic ionic liquid salts, which may be used for exemplification include: (1) two vinyl imidazolium or pyrrolidinium dications separated by an alkyl linkage chain (of various length) or (2) one vinyl imidazolium or pyrrolidinium cation separated an alkyl linkage chain (of various length) and connected to a methyl, ethyl, propyl, or buylimidazolium cation or a methyl, ethyl, propyl, or butylpyrrolidinium cation. The presence of unsaturated groups facilitates cross-linking and/or immobilization.

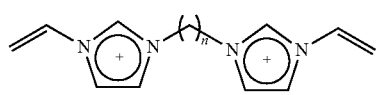

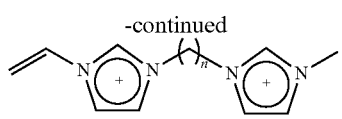

Dianionic anions can also be used with either monocations or dications to form a variety of different ionic liquid combinations. When a dication is used, anyone is used as charge balance must be preserved. The dianionic anions can be of the dicarboxylic acid type (i.e., succinic acid, nonanedioic acid, dodecanedioic acid, etc), as shown below.

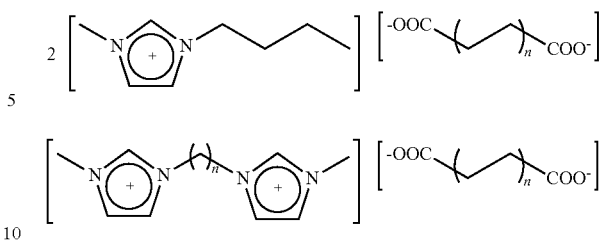

Diionic liquid salts can be coated on a capillary (or solid support) and optionally, subsequently polymerized and/or cross-linked.

In addition to the free radical polymerization of an alkene, other polymerization reactions involving other functional groups either attached to the aromatic ring of the cation, the linkage chain connecting two cations (to form a dication), or the anion can be achieved. Examples of such reactions may include cationic and anionic chain growth polymerization reactions, Ziegler-Natta catalytic polymerization, and step-reaction polymerization. The use of two different monomers to form copolymers through addition and block copolymerization can also be achieved. Additionally, condensation polymerization can be used to connect through functional groups such as amines and alcohols.

Other anions which can be used to form dicationic ionic liquids include, without limitation, triflates, carboxylates, sulfonates and sulfates (both mono- and poly-anionic species). Dianionic ionic liquids can be produced from any dianion which can form a stable salt, preferably which has a melting point below 400° C., more preferably at or below 100° C., most preferably at or below room temperature (25° C.). These include dicarboxylate, disulfonate and disulfates. Mixed dianions, one made from, for example, a dicarboxylate and a disulfate, are also desirable. Cations or counterions for these include, again without limitation, the dications, as well as their monocationic counterparts.

Monoionic and Diionic Liquids

Various monoionic liquid or diionic liquid salt may be used. Diionic liquids such as those shown immediately below can be absorbed or adsorbed onto a solid support.

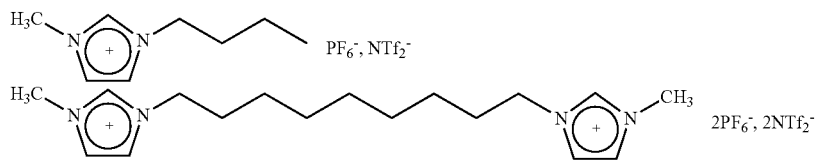

In addition, ionic liquids, both monoionic and diionic liquid salts can be immobilized by being bound or cross-linked to themselves and to a solid support as previously discussed in connection with manufacturing capillary GC columns. To do so, however, the species used should have at least one unsaturated group disposed to allow reaction resulting in immobilization. See for example the monocationic and dicationic species immediately below.

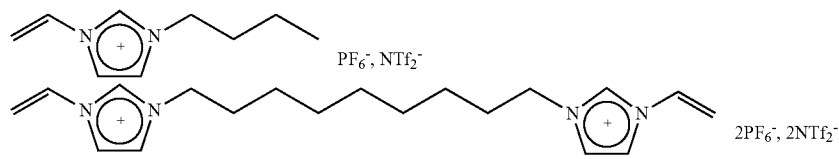

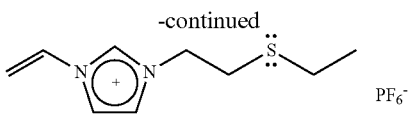

Another type of SPME technique is known as task specific SPME or TSSPME. Task specific SPME allows for the separation or removal, and therefore the detection of particular species. These can include, for example, mercury and cadmium, although the technique is equally applicable to other materials. The concept is exactly the same as previously described with regard to SPME. However, in this instance, the ionic liquids or diionic liquids used are further modified such that they will specifically interact with a particular species. Those shown below, for example, may be used in the detection of cadmium and mercury ($Cd^{2+}$ or $Hg^{2+}$). The first monocationic material can be coated, absorbed or adsorbed onto a fiber as previously discussed. A diionic liquid salt can also be absorbed or adsorbed in known fashion. The second and third ionic liquid materials illustrated below, the first monoionic and the second dicationic, by virtue of the presence of unsaturated groups, can be more easily immobilized on a solid support using techniques analogous to those described previously with regard to cross-linking in connection with manufacturing capillary GC columns.

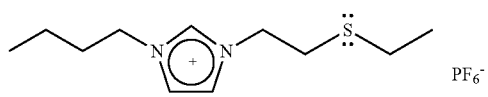

-continued

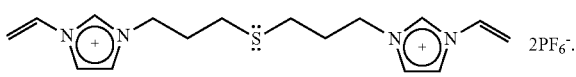

A particular sample can be suspended in a matrix that includes ionic liquids and preferably diionic liquid salts in accordance with the present invention. This matrix can be loaded or immobilized on the fiber of an SPME syringe as described above and then injected into a mass spectrometer to practice a technique known as SPME/MALDI mass spectrometry. The matrix is exposed to a UV laser. This causes the volatilization or release of the sample much as heat does in a GC. This allows the sample to enter mass spectrometer where it can be analyzed. Ionic materials which can be used as a matrix. Non-limiting examples include

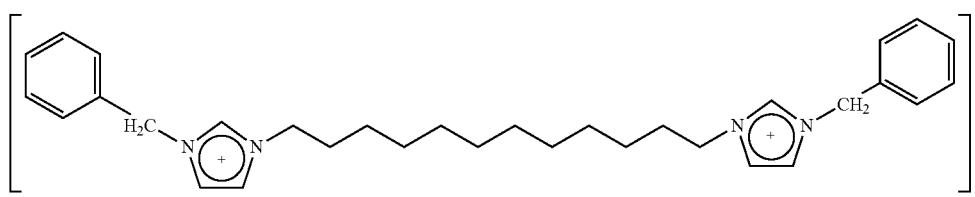

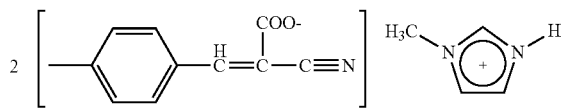

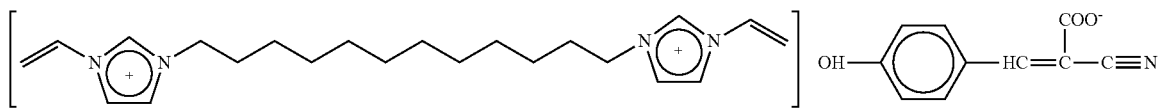

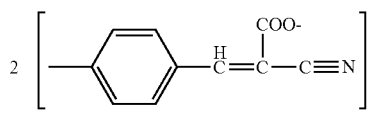

| # | Ionic Liquid | Molecular Weight (g/mol) | Density (g/cm³) | Refractive Index |
|---|---|---|---|---|
| 1 | hvim-NTf$_2$[a] | 459.1 | 1.36 | 1.443 |
| 2 | nvim-NTf$_2$[b] | 501.2 | 1.28 | 1.445 |
| 3 | dvim-NTf$_2$[c] | 543.3 | 1.23 | 1.448 |
| 4 | C$_6$(vim)$_2$-NTf$_2$[d] | 832.1 | 1.53 | 1.449 |
|  | C$_6$vm(im)$_2$-NTf$_2$[e] | 820.1 |  |  |
|  | C$_6$(mim)$_2$-NTf$_2$[f] | 808.1 |  |  |
|  | C$_6$(vim)$_2$-NTf$_2$:C$_6$vm(im)$_2$-NTf$_2$:C$_6$(mim)$_2$-NTf$_2$ 1:2:1 |  |  |  |
| 5 | C$_9$(vim)$_2$-NTf$_2$[g] | 874.3 | 1.47 | 1.457 |
| 6 | C$_{10}$(vim)$_2$-NTf$_2$[h,*] | 888.3 | — | — |

| # | Ionic Liquid | Molecular Weight (g/mol) | Density (g/cm³) | Refractive Index |
|---|---|---|---|---|
| 7 | 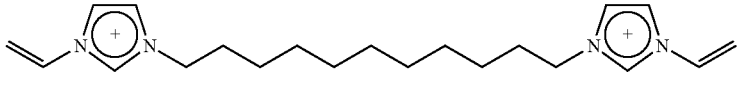<br>2NTf$_2^-$<br>C$_{11}$(vim)$_2$-NTf$_2^i$ | 902.3 | 1.44 | 1.457 |
| 8 | 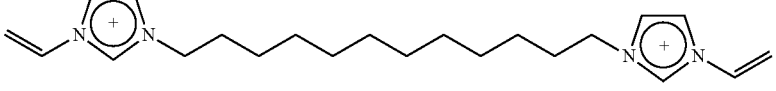<br>2NTf$_2^-$<br>C$_{12}$(vim)$_2$-NTf$_2^{j,*}$ | 916.3 | 1.42 | 1.458 |
| 9 | 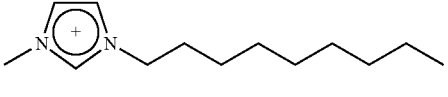<br>NTf$_2^-$<br>nmim-NTf$_2^k$ | 489.3 | 1.30 | 1.434 |

Boron Selective Ionic Liquids and Polymeric Ionic Liquids

In certain embodiments, boron selective ionic liquids are used. A boron selective IL can be comprised of: i) at least one cationic component having at least one functionalized group capable of chelating boron; and, ii) one or more anionic components. In certain embodiments, the functionalized group comprises one or more hydroxyl groups. In other certain embodiments, the functionalized group comprises one or more —(OCH$_3$) hydroxyl groups.

In certain embodiments, the cationic component is polymerized to form a polymeric ionic liquid (PIL).

In certain embodiments, the boron selective ionic liquid IL can include more than one type of ionic component. In one embodiment, the boron selective ionic liquid (IL) can be comprised of at least one saccharide cationic component and one or more anionic components. In certain embodiments, the saccharide cationic component comprises one or more of: polyglycols, monosaccharides, disaccharides, oligosaccharides and polysaccharides, including sugars, starches, cellulose, and related compounds.

In certain embodiments, the cationic component comprises N-methyl-D-glucamine.

In certain embodiments, the cationic component is polymerized to form a polymeric ionic liquid (PIL).

In another broad aspect, there is provided herein a selective polymeric ionic liquid (PIL), comprised of: i) at least one polymerized cationic component having at least one functionalize group capable of chelating boron; and, ii) one or more anionic components.

The boron selective IL and/or PIL is doped with one or more of: non-boron selective ILs and/or PILs, polymeric materials, and solvents.

In another broad aspect, there is provided herein a boron ionic liquid (IL) formed from N-methyl-D-glucamine by the quaternization of an amine using a double nucleophilic substitution with an alkyl halide.

Non-limiting examples of boron selective ILs include:

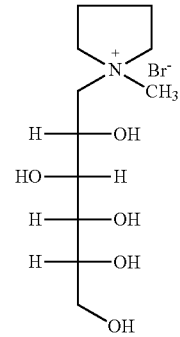

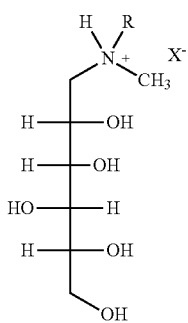

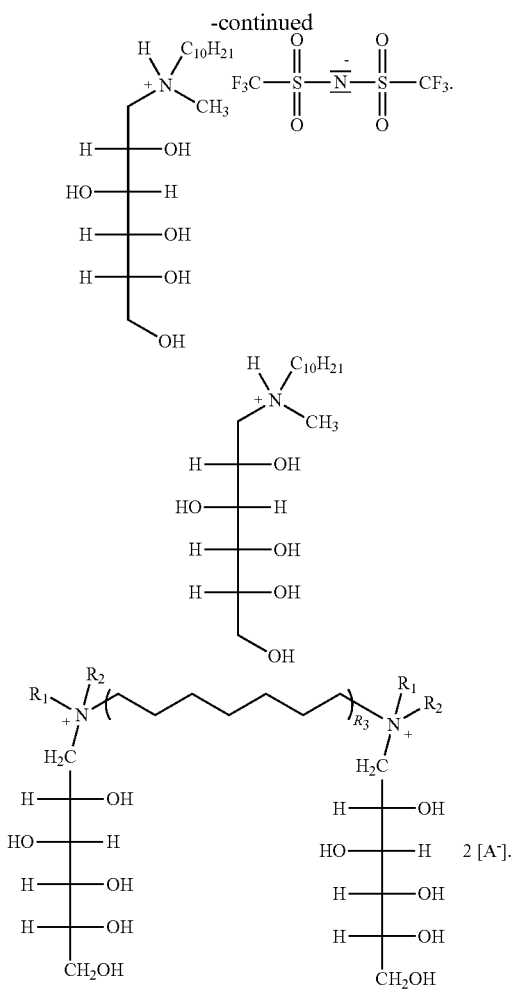

Uses of Photo-Initiated Polymeric Ionic Liquids (P-PILs)

In another broad aspect, there is provided herein a device useful in chemical separation or analysis comprising: a support and at least one P-PIL adsorbed, absorbed or immobilized thereon.

In another broad aspect, there is provided herein a device comprising one or more P-PILs functionalized to: (1) selectively extract one or more analytes of interest and to allow all other analytes to be removed so that one or more pre-concentrated analytes can be separated, identified and/or quantified; and/or (2) to selectively extract all other molecules so that the analyte(s) of interest can be removed from other molecules thereby allowing them to be separated, identified, and/or quantified.

In another broad aspect, there is provided herein a device comprising coated or immobilized P-PILs for solid phase microextraction (SPME), wherein one or more P-PILs are used in neat polymeric form, or mixed with other ILs or P-PILs, solvents, other polymers, including but not limited to PDMS, PEG, silicone oils, or other chromatographic adsorbent materials.

In another broad aspect, there is provided herein a separation device comprising a support at least partially coated with one or more P-PILs.

In another broad aspect, there is provided herein a use of the separation device in one or more of: headspace extraction, direct-immersion extraction, or membrane protected SPME extraction.

One non-limiting example includes where the separation device can be coupled to gas chromatography (GC) in which one or more analytes are thermally desorbed in a GC injection port.

Another non-limiting example includes where the separation device can be coupled to HPLC in which a HPLC mobile phase or buffered component is used to desorb molecules from the support.

Another non-limiting example includes where the separation device can be coupled to capillary electrophoresis (CE) in which a running buffer from the CE is used to remove analytes from the support.

Another non-limiting example includes where one or more analytes to be separated can exist in any forms of matter (solids, liquids, and gases) and can be of any chemical component (small molecules, ions, synthetic or natural polymers, macromolecules, biomolecules).

Another non-limiting example includes where the separation device can be used for applications in liquid-phase microextraction and single drop microextraction.

Non-limiting examples include one or more of the following: the solid support is packed in a chromatographic column; the solid support is a capillary column useful in gas chromatography; the device is use in solid phase microextraction (SPME).

Also provided herein is a device configured for thermally desorbing analytes from the support. In certain embodiments, the device comprises a solvent desorption device coupled to a high performance liquid chromatography column (HPLC).

In certain embodiments, the separation device can comprise one or more of the following: a stationary phase coating on the support; a stationary phase coating coatings for useful for microextractions; a coating for solid phase microextraction (SPME); a support comprising one or more of: a solid fused silica support, a stir bar, a fiber, a film, a membrane, a fibrous mat, a woven or non-woven material.

In another broad aspect, there is provided herein a method comprising mixing one or more P-PILs with one or more solvents to vary the viscosity and surface tension of the P-PIL. In certain embodiments, the method can further include allowing the P-PIL to be suspended from a microsyringe configured for sampling of one or more analytes.

In certain embodiments, at least one suspended drop is used to sample an analyte matrix (liquid, solid, or gas) and wherein the P-PIL is directly injected into a GC, HPLC, or CE or mixed with a solvent and then directly injected into GC, HPLC, or CE. In certain embodiments, the analytes to be separated can exist in any forms of matter (solids, liquids, and gases) and can be of any chemical component, including, but not limited to small molecules, ions, synthetic or natural polymers, macromolecules, biomolecules.

In another broad aspect, there is provided herein a use of at least one P-PIL in an extraction process.

In another broad aspect, there is provided herein a device for selective $CO_2$ absorbance, comprising at least one P-PIL on a support.

In another broad aspect, there is provided herein a device for sequestration of $CO_2$, comprising at least one P-PIL on a support.

In another broad aspect, there is provided herein a process of $CO_2$ capture, comprising using at least one P-PIL as described herein.

In certain embodiments, the process can include being reversible by heating the P-PIL to temperatures around 70-110° C.

In another broad aspect, there is provided herein a device comprising at least one P-PIL on a support, and capable of an on-support metathesis exchange of anions from an immobilized P-PIL absorbent material.

In another broad aspect, there is provided herein a device for extraction of one or more of DNA, RNA, protein, nucleic acids, peptides, amino acids, cellular extracts and portions thereof, comprising at least one P-PIL on a support.

In another broad aspect, there is provided herein a carbon sequestration method, comprising bringing at least one of a reactant gas mixture including carbon dioxide contact with a P-PIL carbon sequestration catalyst at a temperature wherein a solid carbon deposit is formed at the surface of the P-PIL carbon sequestration catalyst.

In a particular embodiment, the method further includes recapturing sequestered $CO_2$ and reusing the P-PIL carbon sequestration catalyst.

In certain embodiments, the method can further include tuning one or more of chemical and physical properties of the P-PIL through one or more of: i) choice of the anion, and ii) modification of the cation structure.

In certain embodiments, the method can further include tuning one or more of chemical and physical properties of the P-PIL through one or more of: i) choice of the cation, and ii) modification of the ion structure.

In certain embodiments, the method can further include forming a mixture of P-PIL and one or more extraction additives or phase modifiers that aid in selectively increasing extraction efficiency or promoting wetting of glass or metal substrates.

In certain embodiments, the solid phase microextraction material can include ionic liquids that are comprised of one or more of non-molecular ionic solvents comprised of bulky, asymmetric cations paired with one or more types of anions. In certain embodiments, one or more of chemical and physical properties of the P-PILs are capable of being tunable through choice of anion and/or modification of the cation structure.

In another broad aspect, there is provided herein a use of P-PILs in developing one or more task-specific ionic liquids (TSILs) of microextraction coatings, chromatographic media, membrane systems, and chemical sensors.

In another broad aspect, there is provided herein a composite semipermeable device, comprising: a porous substrate comprised of at least one P-PIL on a support; and a separating functional IL material layer formed on the substrate film, wherein the IL that forms the separating functional layer contains a boron selective IL and/or PIL.

In another broad aspect, there is provided herein a semipermeable membrane element, comprising the separation device described herein as a separation membrane.

In another broad aspect, there is provided herein a fluid separation system, comprising the separation device described herein as a fluid separation element.

In another broad aspect, there is provided herein a water treatment method, comprising subjecting water to a permeation process using the separation device described herein.

In another broad aspect, there is provided herein a method of purifying water comprising: providing a feed water to a filtration device comprised of the separation device described herein. In certain embodiments, the feed water is seawater, brackish water or oil field recovery water. In certain embodiments, the method can further include reducing boron content in the feed water to less than about 0.5 mg/L.

In another broad aspect, there is provided herein use of the compound described herein for extraction of boron from a feed water.

In another broad aspect, there is provided herein use of the compounds described herein as a solvent for a stereoselective reaction.

In another broad aspect, there is provided herein use of the compound described herein for one or more of: a stationary phase for chiral separation in gas chromatography, high performance liquid chromatography, and as a running buffer modifier for capillary electrophoresis.

In certain embodiments, the separation coefficient of boric acid between water and the boron compounds described herein can be done by liquid-phase extraction coupled with spectrophotometry or atomic spectroscopy, as well as the possibility to regenerate the ionic liquid by rinsing with an acidic or basic aqueous solution or by subjecting the IL/PIL material to electrodialysis.

Making a Cationic Polymeric Ionic Liquid (C-P-PIL)

In another broad aspect, there is a method of making a photo-initiated polymeric ionic liquid (P-PIL) coated support, comprising:
  i) mixing at least one ionic liquid monomer (IL) with at least one photo-initiator,
  ii) at least partially coating a support with the mixture of step i), and
  iii) exposing the coated support of step ii) to UV light to form a cationic photo-initiated polymeric ionic liquid (c-P-PIL) coated support,
  where the c-P-PIL comprises:
    at least one ionic component comprised of anionic liquid (IL), and
    one or more mobile cationic components, wherein the cationic components can be the same or different.

It is to be understood that the c-P-PIL can be formed by one or more of polymerization reactions that include one or more of: cationic and anionic chain growth polymerization reactions, Ziegler-Natta catalytic polymerization, and step-reaction polymerization; use of two different monomers to form copolymers through addition and/or block copolymerization.

The method can further include adding at least one cross-linker to the mixture of step i).

Also, in certain embodiments, at least a portion of a surface of the support is functionalized prior to coating with the IL monomer mixture. For example, at least a portion of a surface of the support is functionalized by etching prior to coating with the IL monomer mixture, ad described herein.

As used herein, "polymeric anion" generally refers to a polymer which has a negative ionic charge. Non-limiting examples of polymeric anions can include: anions of polymeric carboxylic acids, such as polyacrylic acids, polymethacrylic acids or polymaleic acids, or polymeric sulfonic acids, such as polystyrene sulfonic acids and polyvinyl sulfonic acids. The polycarboxylic and -sulfonic acids can also be copolymers of and vinyl sulfonic acids with other polymerizable monomers, such as acrylic acid esters and styrene.

Non-limiting specific examples can include: polyacrylate, polymethacrylate, dextran, sulfate, sulfated glycosaminoglycans, polyglutamate, polyaspartate, carboxymethyl-cellulose, -dextran, or -agarose, sulfoethyl- or sulfopropylcellulose, -dextran, or -agarose, polyphosphate, polyanethole sulfonate, or any other suitable negatively charged polymer. Specific non-limiting examples of polymeric anions can include: anions of polymeric carboxylic acids (e.g., polyacrylic acids, polymethacrylic acid, polymaleic acids, etc.); polymeric sulfonic acids (e.g., polystyrene sulfonic acids ("PSS"), polyvinyl sulfonic acids, etc.); and the like. The acids may also be copolymers, such as copolymers of vinyl carboxylic and vinyl sulfonic acids with other polymerizable monomers, such as acrylic acid esters and styrene. Non-limiting examples of monomeric anions include, for example, anions of $C_1$ to $C_{20}$ alkane sulfonic acids (e.g., dodecane sulfonic acid); aliphatic perfluorosulfonic acids (e.g., trifluoromethane sulfonic acid, perfluorobutane sulfonic acid or perfluorooctane sulfonic acid); aliphatic $C_1$ to $C_{20}$ carboxylic acids (e.g., 2-ethyl-hexylcarboxylic acid); aliphatic perfluorocarboxylic acids (e.g., trifluoroacetic acid or perfluorooctanoic acid); aromatic sulfonic acids optionally substituted by $C_1$ to $C_{20}$ alkyl groups (e.g., benzene sulfonic acid, o-toluene sulfonic acid, p-toluene sulfonic acid or dodecylbenzene sulfonic acid); cycloalkane sulfonic acids (e.g., camphor sulfonic acid or tetrafluoroborates, hexafluorophosphates, perchlorates, hexafluoroantimonates, hexafluoroarsenates or hexachloroantimonates); and so forth. In certain embodiments, the polymeric anions can be one or more of: a polymeric carboxylic or sulfonic acid (e.g., polystyrene sulfonic acid ("PSS"); for example, where the molecular weight of such polymeric anions typically ranges from about 1,000 to about 2,000,000, and in some embodiments, from about 2,000 to about 500,000.

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference herein.

EXAMPLE 1

Photo-Initiation of Polymeric Ionic Liquids
Materials
1-vinylimidazole, 1,8-dibromooctane, 1,4-dibromooctane, 1,12-dibromododecane, vinyltrimethoxysilane (VTMS), 2,2'-azobisisobutyronitrile (AIBN), 1-chlorohexane, ammonium hydrogen difluoride, and 2-hydroxy-2-methylpropiophenone (HMPP) were purchased from Sigma-Aldrich (Milwaukee, Wis., USA).

Analytes chosen including 2-methyl-1-butanol, cyclohexanol, octanol, furfural, benzaldehyde, 1-phenyl-1-propanol, ethyl propionate, ethyl hexanoate, ethyl valerate, furfural pentanoate, and furfural propionate were purchased from Sigma-Aldrich. Acetonitrile, acetone, chloroform, methanol, n-hexane, isopropanol, dichloromethane, and ethyl acetate were purchased from Fisher Scientific (Fair Lawn, N.J., USA). Ultrapure water (18.2 MΩ/cm) was obtained from a Milli-Q water purification system (Millipore, Bedford, Mass., USA) and was used for the preparation of all aqueous solutions. Homemade SPME fibers consisting of untreated fused silica capillary tubing (0.5 mm I.D) and a 10 μL Hamilton syringe were purchased from Supelco (Bellefonte, Pa.) and Hamilton (Reno, Nev., USA), respectively. Amber glass vials (20 mL) with PTFE/Butyl septa caps were purchased from Supelco. The RPR-100 UV reactor was purchased from Southern New England Ultraviolet Company (Bradford, Conn.).

Methods
The ionic liquid (IL) monomer, 1-vinyl-3-hexyl imidazolium chloride ([VHIM][Cl]), was synthesized. Briefly, 0.05 mol of 1-vinylimidazole was reacted with 0.075 mol of 1-chlorohexane in 15 mL of isopropanol at 70° C. for 72 h. The reaction yielded [VHIM][Cl], which was purified by dissolving in 30 mL of water and extracted six times with 10 mL aliquots of ethyl acetate. The water layer containing the IL monomer was recovered and dried under vacuum at 70° C. for 2 days. The purity of the monomer was confirmed using $^1$H nuclear magnetic resonance ($^1$H NMR) and electrospray ionization-mass spectrometry (ESI-MS).

The synthesis of the di-cationic cross-linkers, namely, 1-8-Di (3-vinylimidazolium) octane dibromide ([DiVOIM][Br$_2$]), and 1-12-Di (3-vinylimidazolium) dodecane dibromide ([DiVDDIM][Br$_2$]) were carried out. [DiVOIM][Br$_2$] was synthesized by reacting 2 molar equivalence of 1-vinylimidazole with 1 molar equivalence of 1,8-dibromooctane in 5 mL of isopropanol at 50° C. for 36 hr in a dark environment. The di-cationic product was then purified by water and ethyl acetate, and was dried under vacuum at 50° C. for 2 days. The [DiVDDIM][Br$_2$] cross-linker was synthesized analogous to its octyl counterpart, however, the reagents were refluxed in 15 mL of isopropanol. The purity of the cross-linkers was confirmed using $^1$H NMR and ESI-MS.

Homemade SPME fibers were prepared. Briefly, untreated fused silica capillary tubing was epoxy-glued to the plunger of a disassembled Hamilton syringe. Subsequently, 1 cm of the capillary was flame-treated to remove the polyimide coating and its tip flame-sealed. The bare fiber was then washed with acetone, methanol, methylene chloride, and hexane and conditioned in a GC injector at 250° C. for 5 min.

Pretreatment of Support
In the examples described herein the support comprised fibers. A series of fiber modification steps were employed prior to coating the [VHIM][Cl] monomer, cross-linker, and initiator mixture in order to establish a stable film of this mixture on the fiber surface.

Figure 6:
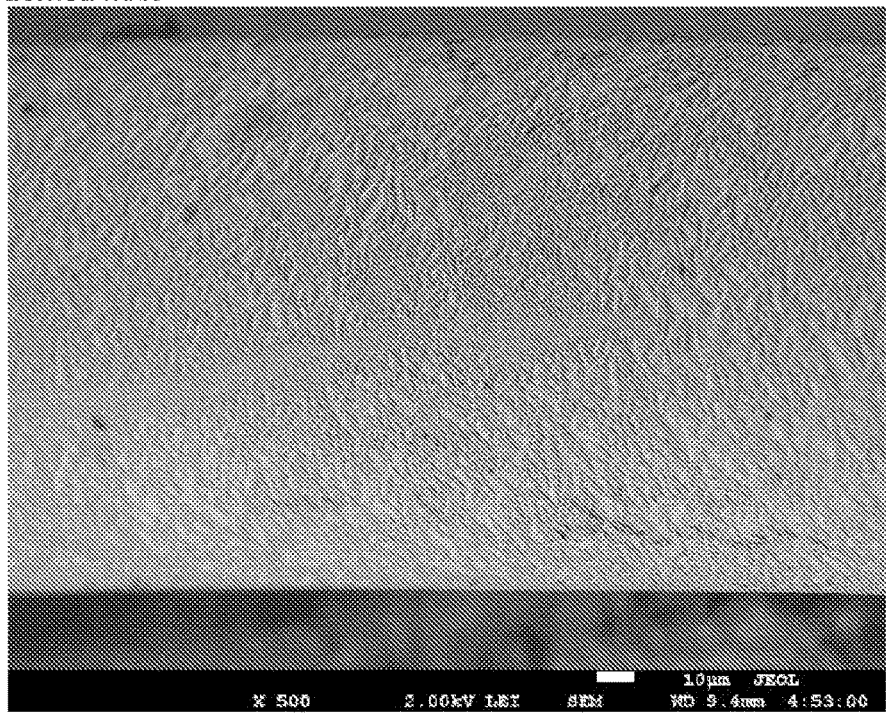
FIG. 6: SEM photograph of etched fiber.

The bare fiber was etched (See FIG. 6). In brief, the 1 cm bare silica portion was immersed into a 5% (w/v) ammonium hydrogen difluoride solution in methanol for 5 min, air dried for 30 min, and conditioned in a GC injector at 250° C. for 1 hr. The fiber was then washed thoroughly with water to remove excess salt and conditioned in a GC injector at 250° C. for 5 min.

Figure 7:
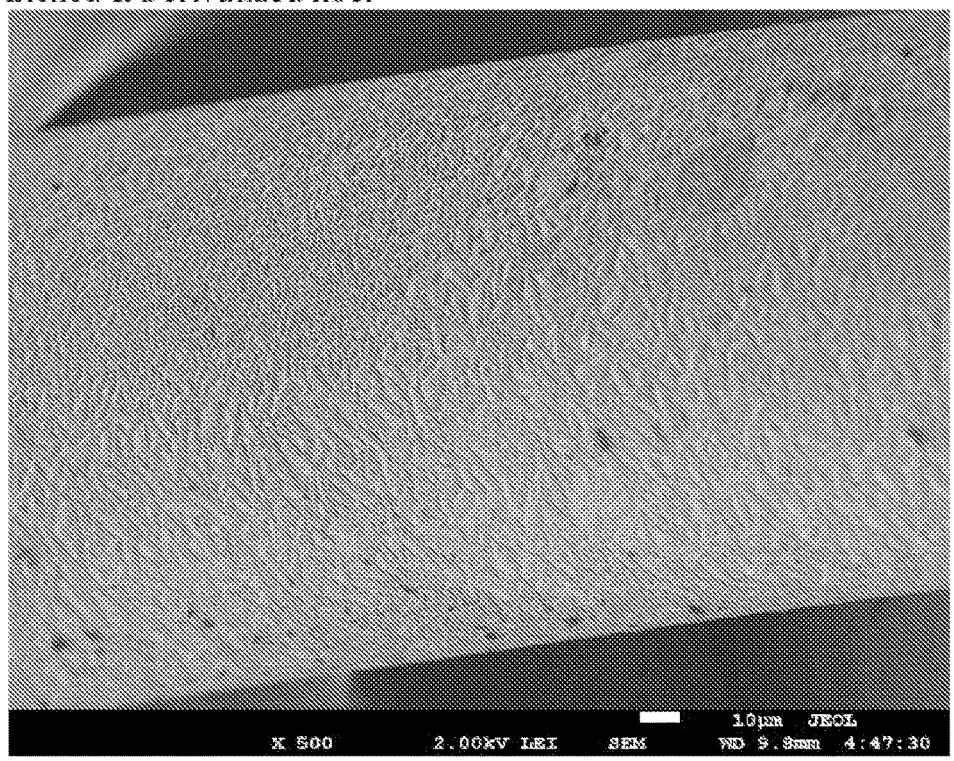
FIG. 7: SEM photograph of etched and derivatized fiber.

To facilitate the covalent bonding of the IL/cross-linker mixture to the surface and further enhance the chemical stability of the coating, the etched fiber was immersed into 10 mL of a VTMS solution to functionalize the surface with a vinyl substituent prior to coating. (See FIG. 7). Characterization of the etched and functionalized fiber was performed using scanning electron microscopy (SEM) and energy-dispersive X-ray spectroscopy (EDX).

IL Mixtures
Varying amounts of cross-linker, initiator, and IL monomer mixtures were prepared. Coating mixtures were prepared by dissolving 0, 15, 30, or 50% (w/w) of a cross-linker in neat [VHIM][Cl] monomer. The composition of each copolymer coating prepared and their respective naming system are provided in Table 1, below:

TABLE 1

| sorbent coating abbreviation | cross-linker | percentage cross-linker[a] (w/w) | initiator | percentage initiator[a] (w/w) | polymerization approach | approximate film thickness (μm) |
|---|---|---|---|---|---|---|
| Fiber AIBN | | | AIBN[b] | 2 | thermal | 4 |
| Fiber UV | | | DAROCUR 1173[c] | 3 | UV | 4 |
| Fiber 1 | | | DAROCUR 1173 | 1 | UV | 7 |
| Fiber 2 | $[(VIM)_2C_8]2[Br]$ | 15 | DAROCUR 1173 | 3 | UV | 3 |
| Fiber 3 | $[(VIM)_2C_8]2[Br]$ | 15 | DAROCUR 1173 | 1 | UV | 6 |
| Fiber 4 | $[(VIM)_2C_8]2[Br]$ | 30 | DAROCUR 1173 | 3 | UV | 7 |
| Fiber 5 | $[(VIM)_2C_8]2[Br]$ | 30 | DAROCUR 1173 | 1 | UV | 4 |
| Fiber 6 | $[(VIM)_2C_8]2[Br]$ | 50 | DAROCUR 1173 | 3 | UV | 7 |
| Fiber 7 | $[(VIM)_2C_{12}]2[Br]$ | 50 | DAROCUR 1173 | 1 | UV | 4 |
| Fiber 8 | $[(VIM)_2C_{12}]2[Br]$ | 15 | DAROCUR 1173 | 3 | UV | 3 |
| Fiber 9 | $[(VIM)_2C_{12}]2[Br]$ | 30 | DAROCUR 1173 | 1 | UV | 7 |
| Fiber 10 | $[(VIM)_2C_{12}]2[Br]$ | 30 | DAROCUR 1173 | 3 | UV | 9 |
| Fiber 11 | $[(VIM)_2C_{12}]2[Br]$ | 50 | DAROCUR 1173 | 1 | UV | 4 |
| Fiber 12 | $[(VIM)_2C_{12}]2[Br]$ | 50 | DAROCUR 1173 | 3 | UV | 7 |

[a] Relative to the mass of the [VHIM][Cl] IL monomer.
[b] 2,2'-azobis(2-methylpropionitrile).
[c] 2-hydroxy-2-methylpropiophenone.

In certain embodiments, the [DiVOIM][$Br_2$] cross-linker possessed higher solubility, compared to its longer-chained counterpart, in the [VHIM][Cl] monomer and can be fully-dissolved at room temperature.

Figure 8:
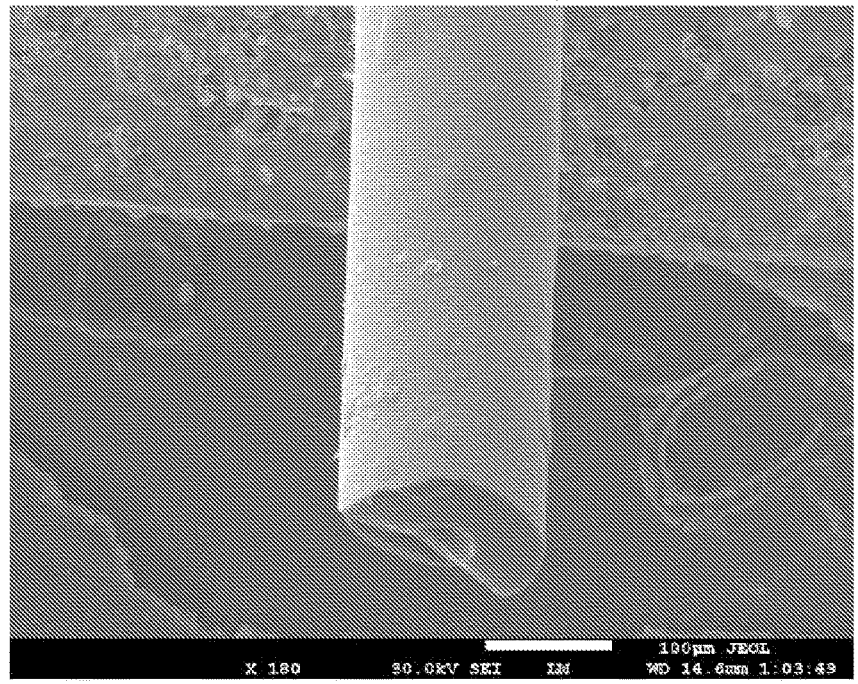
FIG. 8: SEM photograph of etched and derivatized fiber smeared with monomer.

The [DiVDDIM][$Br_2$]/[VHIM][Cl] monomer mixture was heated to 40° C. for 10 min followed by vigorous stirring in order to enhance its solubility. Subsequently, 1 or 3% of the HMPP initiator was added to the mixture. The coating mixture was evenly applied to the derivatized fiber via a coating process. (See FIG. 8). The coated fibers were then subjected to UV-initiated free-radical polymerization at a 254 nm UV-wavelength for 2 hr. Following polymerization, each fiber was exposed to the GC injector at 175° C. for 5 min to monitor bleeding of the sorbent coating. This process was repeated four times for each fiber. Thermal gravimetric analysis (TGA) was used to characterize the IL monomeric mixtures and cross-linked PIL sorbent coatings.

Testing of P-PIL Coated Supports

In order to prepare working standards, the volatile alcohol, aldehydes, and esters (VAAEs) were dissolved individually in acetonitrile at a concentration of 40 mg $mL^{-1}$. A stock solution was prepared from the individual stock solutions by combining all analytes at various concentrations and diluting with acetonitrile. A working standard with analyte concentrations ranging from 10 to 500 ppb was prepared by spiking a specific volume of the standard stock solution into a 20 mL amber sampling vial filled with 15 mL of a 30% NaCl (w/v) aqueous solution. Extractions in headspace mode were performed by exposing the fiber coating to the headspace of the sampling vial capped with a PTFE/Butyl self-sealing septa screw cap at room temperature. Agitation was performed at 750 RPM using a magnetic stir bar.

Following a 45 min extraction time, the analytes were desorbed into the GC-MS by exposing the fiber to the GC injector at 175° C. for 5 min. Direct immersion studies were also performed in a similar manner; however, 20 mL of a de-ionized water solution was used as a sample matrix. Used sampling vials and stir bars were cleaned by sonication in a detergent solution, followed by de-ionized water and acetone for 1 hr each. Carryover was monitored regularly and deemed to be less than 5%.

Fiber bleeding, precision, and extraction efficiency tests for all fiber coatings were performed using an Agilent 7890 gas chromatograph coupled to a 5975 mass spectrometer (GC-MS). Detection of all analytes via single ion monitoring (SIM) mode were established by monitoring 2 to 3 relevant m/z fragments for each analyte. Helium was used as a carrier gas with a flow rate of 1 mL $min^{-1}$ while a HP5-MS (30 m×250 μm×0.25 μm) GC column was employed for all studies. The thermal desorption of analytes as well as the bleed-monitoring were performed in splitless mode.

Separation for all fiber bleeding experiments was achieved using the following temperature program: initial temperature was set to 75° C. and held for 6 min. The temperature was then increased to 280° C. at 10° C. $min^{-1}$ and held for 10 min. Separation of all analytes in the extraction studies was achieved by using the following temperature program: initial temperature was set to 70° C. and held for 6 min. The temperature was increased to 150° C. at 20° C. $min^{-1}$. Then, the temperature was increased to 280° C. at 10° C. $min^{-1}$ and held for 10 min.

As seen in FIGS. 6-13, the sorbent coating remained smooth and intact after UV polymerization. Immersion of the cross-linked PIL sorbent coating in various solvents including chloroform, methylene chloride, dimethyl sulfoxide, and water under high agitation showed no visible loss of coating by optical microscopy.

Thermal stability of sorbent coatings should be investigated to determine the appropriate desorption temperature for purposes of maximizing the fiber lifetime. For imidazolium-based ILs possessing halide ions, thermal stability is governed by their susceptibility to undergo nucleophilic substitution at high temperatures. Thermal stabilities of the copolymers synthesized in this example were monitored by thermal gravimetric analysis (TGA). The TGA curves for copolymers derived from the monocationic [VHIM][Cl] IL containing different amounts of the [(VIM)$_2$C$_{12}$] 2[Br] dicationic IL cross-linker are compared to the linear poly ([VHIM][Cl]) PIL prepared by AIBN-initiated polymerization containing no cross-linker. The cross-linked PILs produced by UV polymerization exhibited slightly higher stability than the AIBN-initiated PIL sorbent coating. As the extent of cross-linking was increased, the thermal stability also increased. Without wishing to be bound by theory, the enhancement in the copolymer thermal stability is believed to be the result of adding cross-linkers containing the less thermally labile bromide anion. A noncross-linked UV-initiated poly([VHIM][Cl]) PIL coating was also examined, wherein this coating exhibited lower thermal stability compared to its AIBN-initiated counterpart.

The addition of kosmotropic salts significantly increased the extraction efficiency. The extraction efficiency of all analytes increased with increasing salt concentration. Many analytes exhibited over an order of magnitude increase in extraction efficiency at 30% NaCL (w/v) compared to when no salt was added; therefore, this concentration was used for the subsequent headspace SPME studies.

Sorption-time profiles were generated for Fiber 6 and Fiber 12 (see Table 1) in headspace mode and Fiber 12 in the direct immersion mode. For headspace SPME, the profiles were obtained by exposing the fiber for different time intervals to the headspace of the sample solution containing the selected analytes in a 30% NaCl (w/v) solution at varying concentrations. For most analytes, equilibration was achieved at approximately 45 min except for 1-octanol and α-ethyl benzene methanol in which equilibration was achieved in approximately 60 min. In the case of Fiber 12, equilibration times were also reached at approximately 45 min for most analytes. Sorption time optimization for direct immersion studies was performed by immersing Fiber 12 in a deionized water sample solution at various time intervals and analyte concentrations. Most analytes achieved equilibration at approximately 45 min.

Figure 9:
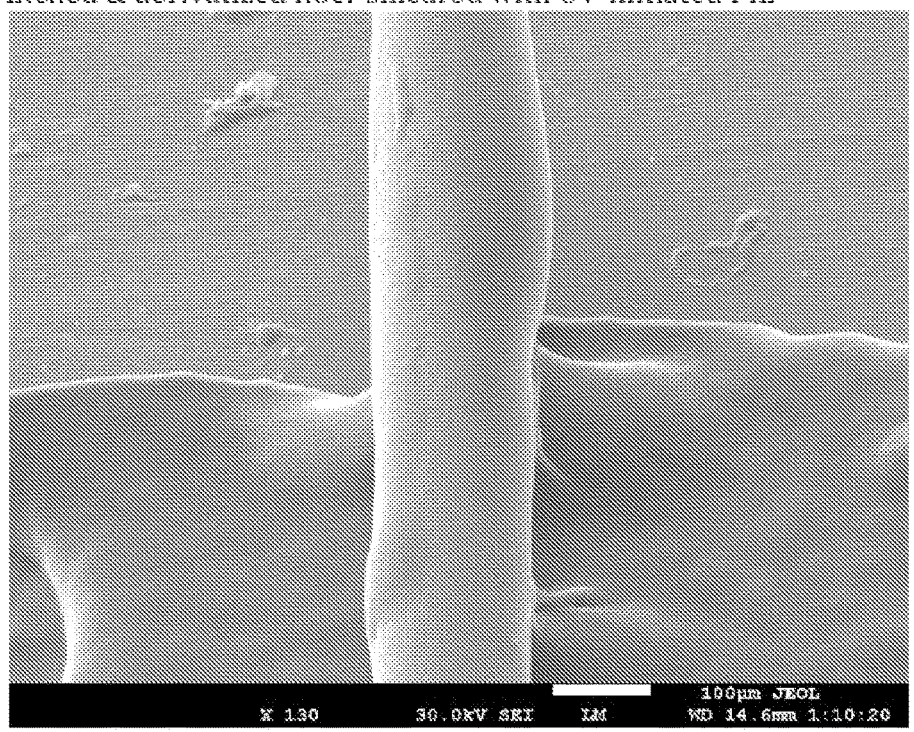
FIG. 9: SEM photograph of etched and derivatized fiber smeared with UV-initiated polymeric ionic liquid (P-PIL).

FIG. 9 shows a SEM photograph of etched and derivatized fiber smeared with UV-initiated polymeric ionic liquid (P-PIL).

Figure 10:
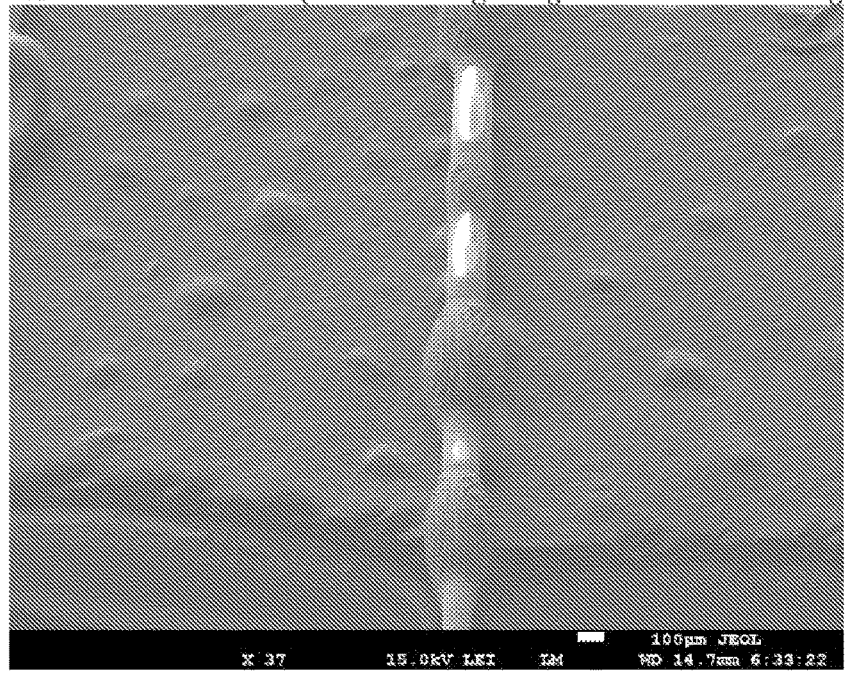
FIG. 10: SEM photograph of etched and derivatized fiber with 5% C8 cross-linker photo-initiated polymeric ionic liquid (P-PIL) (smear coating using 4 hr oven-dried coating solution).

FIG. 10 shows a SEM photograph of etched and derivatized fiber with 5% C8 cross-linker P-PIL (smear coating using 4 hr oven-dried coating solution).

Figure 11:
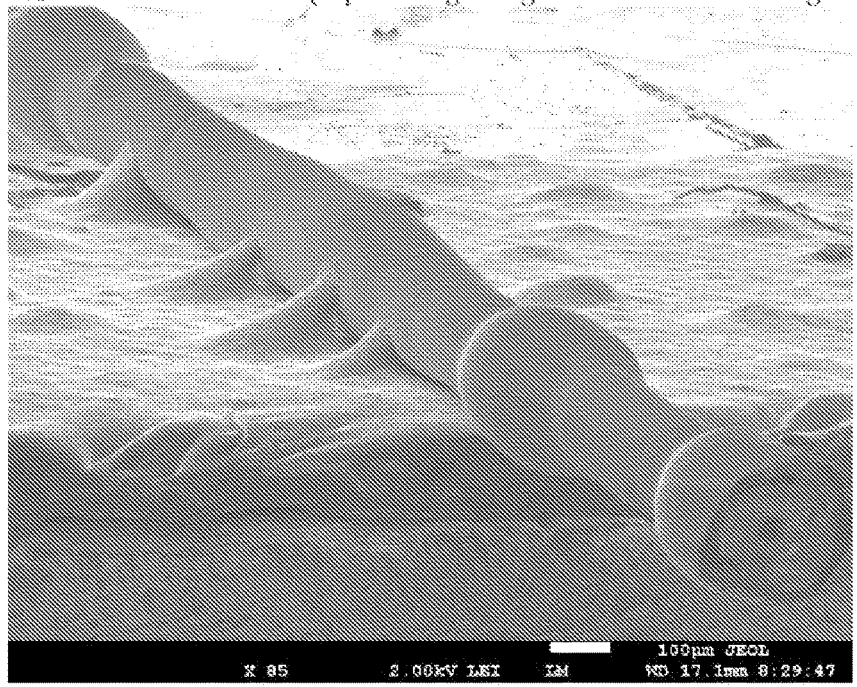
FIG. 11: SEM photograph of etched and derivatized fiber with 5% C8 cross-linker P-PIL (dip coating using 4 hr oven-dried coating solution).

FIG. 11 shows a SEM photograph of etched and derivatized fiber with 5% C8 cross-linker P-PIL (dip coating using 4 hr oven-dried coating solution).

Figure 12:
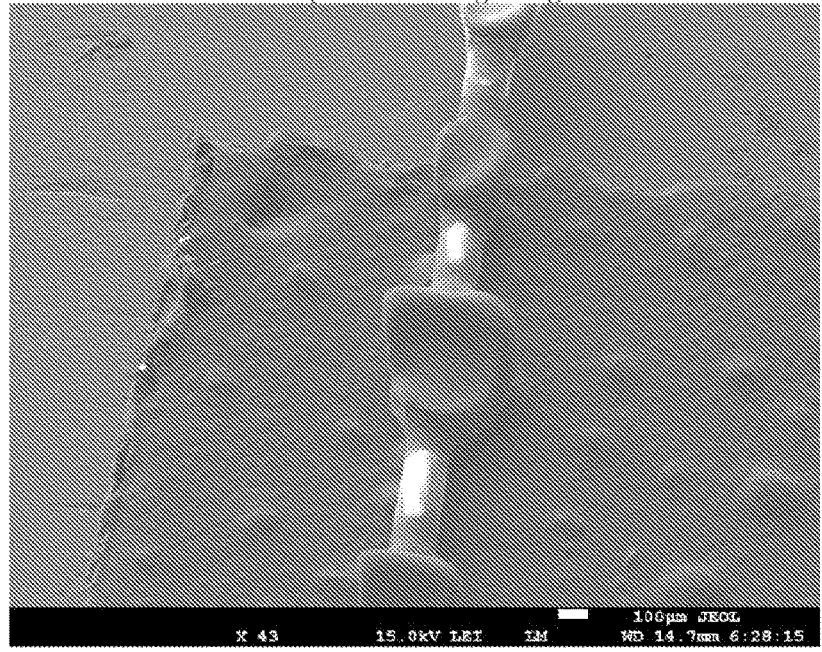
FIG. 12: SEM photograph of etched and derivatized fiber with 15% C8 cross-linker P-PIL (smear coating using 4 hr oven-dried coating solution).

FIG. 12 shows a SEM photograph of etched and derivatized fiber with 15% C8 cross-linker P-PIL (smear coating using 4 hr oven-dried coating solution).

Figure 13:
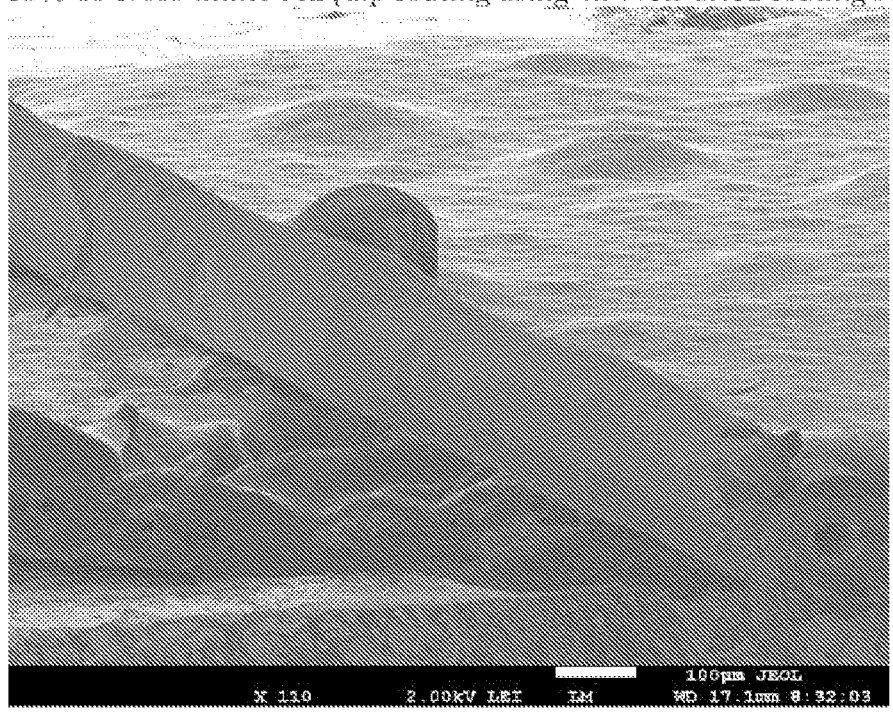
FIG. 13: SEM photograph of etched and derivatized fiber with 15% C8 cross-linker P-PIL (dip coating using 4 hr oven-dried coating solution).

FIG. 13 shows a SEM photograph of etched and derivatized fiber with 15% C8 cross-linker P-PIL (dip coating using 4 hr oven-dried coating solution).

Figure 14:
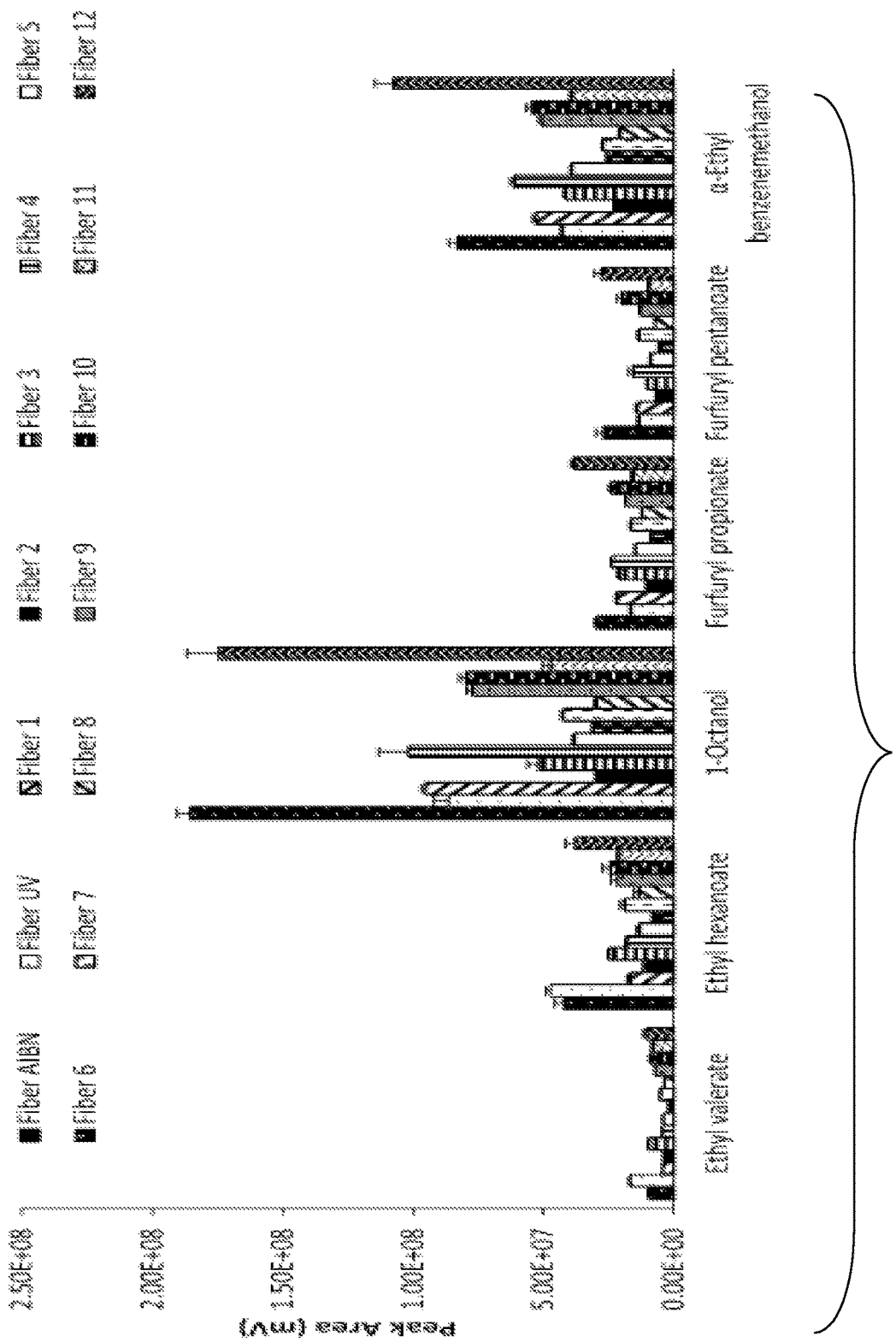
FIG. 14: Comparison of the extraction efficiency for selected sorbent coatings in headspace SPME mode.
Figure 15A:
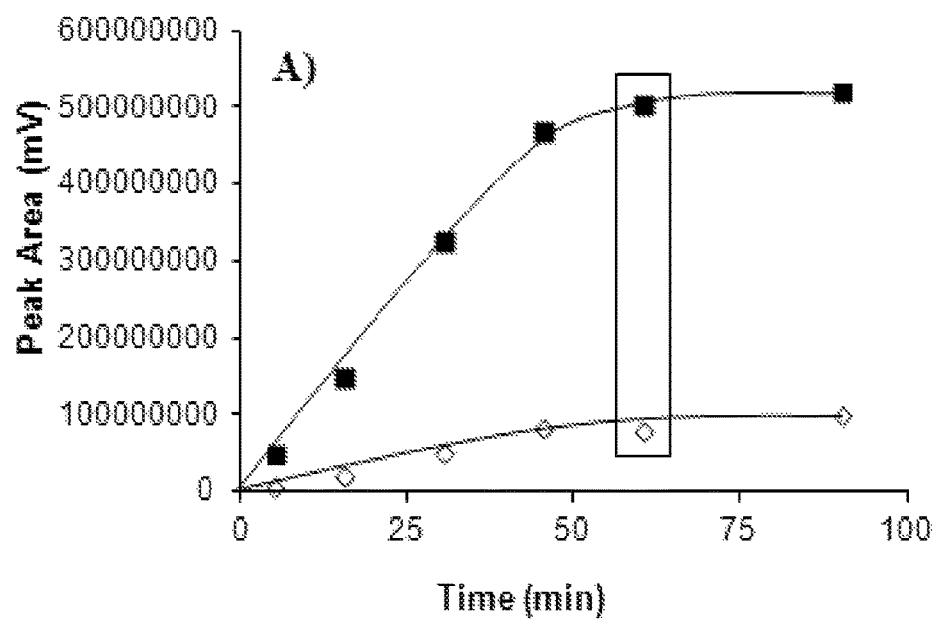
FIGS. 15A-F: Sorption time profile for naphthalene and 1-octanol at 10 µg L$^{-1}$ and 100 µg L$^{-1}$, respectively. Rectangles indicate the sorption time chosen for subsequent competitive inhibition studies. A) PDMS/DVB; B) PA; C) Fiber PIL 1; D) Fiber PIL 2; E) Fiber PIL 3; F) Fiber PIL 4.
Figure 15B:
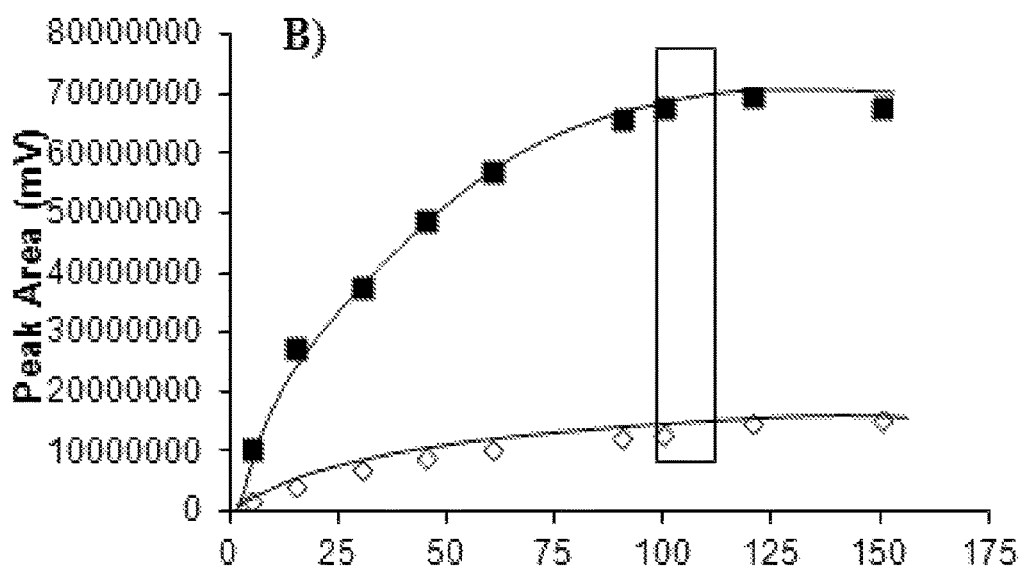
Figure 15C:
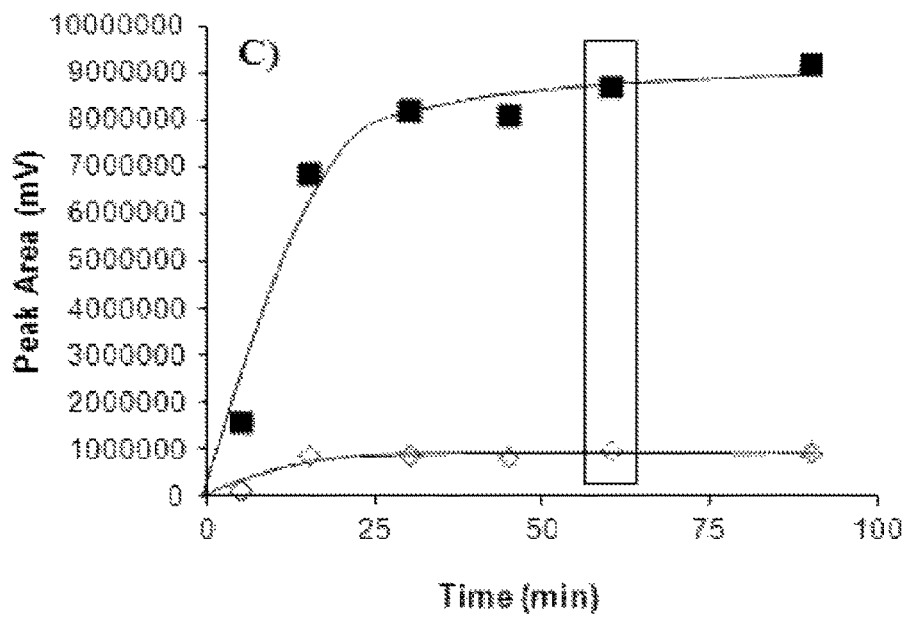
Figure 15D:
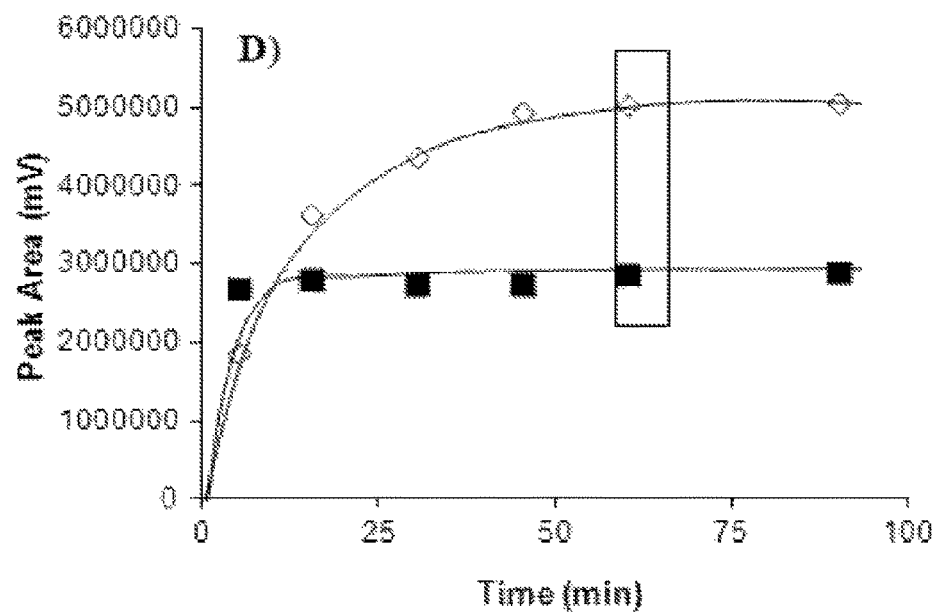
Figure 15E:
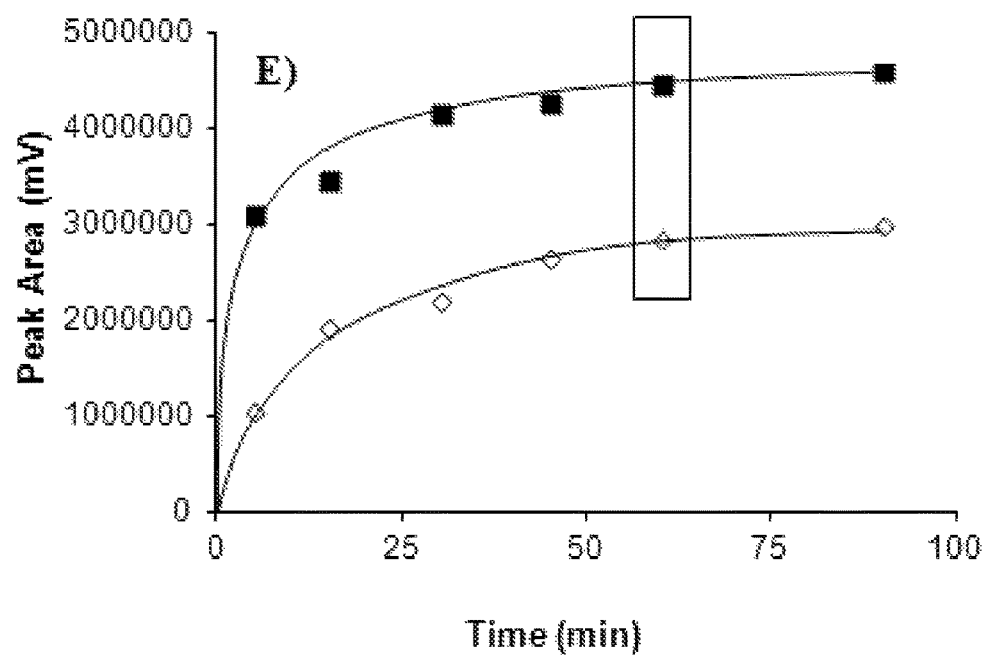
Figure 15F:
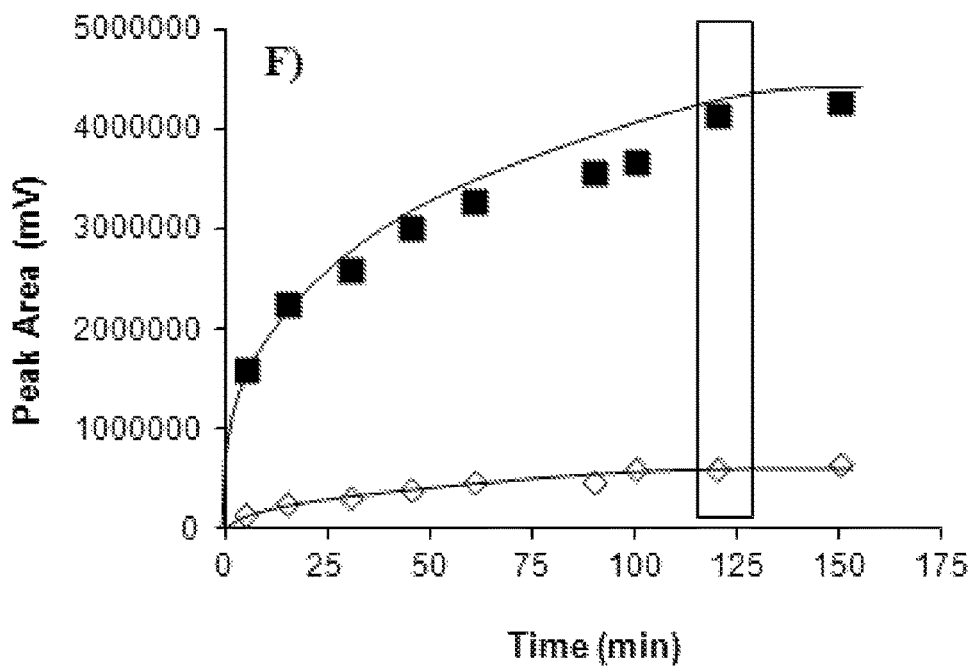

To understand the effects of copolymerizing PIL cross-linkers with the [VHIM][Cl] IL monomer in terms of analyte extraction efficiency, various dicationic IL cross-linker and monocationic IL monomer compositions were compared. This comparison is illustrated in FIG. 14, which displays the extraction efficiency for all fourteen fibers prepared in this example in headspace SPME mode. Coatings with varying amounts of cross-linker to monomer (15, 30, and 50% w/w), cross-linker type [(VIM)$_2$C$_8$] 2[Br] and [(VIM)$_2$C$_{12}$] 2[Br]), and initiator content (1 or 3% w/w relative to the [(VHIM)] [Cl] IL monomer) were prepared and subjected to headspace extraction of chosen analytes.

The PIL-based coatings containing [(VIM)$_2$C$_8$] 2[Br] cross-linker revealed a few general trends. The extraction efficiency of all analytes was lowest for Fiber 2 and Fiber 6 compared to other cross-linked coatings containing the [(VIM)$_2$C$_8$] 2[Br] cross-linker. For the coatings containing 15% and 50% (w/w) of the [(VIM)$_2$C$_8$] 2[Br] IL cross-linker, the lower amount of initator (1%) appears to provided a higher extraction efficiency compared to the higher initiator content. An opposite trend is observed when comparing Fiber 3 with Fiber 4, except in the case of ethyl valerate and ethyl hexanoate. Keeping the amount of initiator constant, a variation in the weight percentage of the [(VIM)$_2$C$_8$] 2[Br] IL cross-linker within the copolymer also affected the extraction efficiency. For example, Fiber 1 provided higher peak areas for 1-octanol compared to Fiber 3. The difference was less significant in the case of aldehydes and esters. Additionally, Fiber 3 resulted in better extraction efficiency for most analytes compared to Fiber 5. On the other hand, when using 3% w/w initiator, Fiber 4 showed higher peak areas than Fiber 2 and Fiber 6, which exhibited similar extraction efficiencies to one another. The film thickness of a coating influences the amount of analyte extracted. Because the film thickness of all coatings in this example was approximately 3 to 9 μm, the difference may cause some variation in the observed extraction performance.

A few trends were also observed for PIL coatings containing the [(VIM)$_2$C$_{12}$] 2[Br] IL cross-linker. When using 1% (w/w) initiator, Fiber 9 possessed comparable extraction efficiency to Fiber 11 for aldehydes and esters. In the extraction of alcohols, however, Fiber 9 outperformed its higher cross-linked counterpart, especially in the case of 1-octanol. Fiber 7, the 15% cross-linked copolymer, typically extracted similar amounts of analyte compared to Fiber 11, the 50% cross-linked copolymer, with minor variations for a few analytes. Similar to the [(VIM)$_2$C$_8$] 2[Br] cross-linked PILs, Fiber 7 (containing 1% (w/w) initiator) exhibited higher extraction efficiency for all analytes compared to Fiber 8, which contained 3% (w/w) initiator). When the amount of cross-linker was increased to 30% and 50%, higher peak areas were observed for coatings consisting of 3% (w/w) initiator relative to 1%. In a comparison of the cross-linkers, Fiber 12, consisting of a 50% (w/w) [(VIM)$_2$C$_{12}$] 2[Br] cross-linker, outperformed Fiber 6, for all analytes especially 1-octanol, in which 3-fold higher peak areas were observed.

To evaluate the selectivity and sensitivity of the cross-linked PIL coatings, calibration curves were constructed for six representative fibers, namely, Fibers AIBN, UV, 4, 6, 10, and 12. These coatings were selected to investigate the effect of cross-linker added in the copolymer on overall analytical performance. All coatings chosen were produced using 3% (w/w) initiator, as it was observed that many of these coatings produced higher extraction efficiencies compared to copolymers made using 1% initiator. Calibration curves were generated by decreasing the analyte concentration from 500 to 0.1 μg L$^{-1}$ using a minimum of seven calibration levels. Headspace extractions were performed from an aqueous solution containing 30% (w/v) NaCl at room temperature with an extraction time of 45 min under agitation. The following Table 2 lists the figures of merit for the four cross-linked PIL coatings:

TABLE 2

Figures of Merit of Selected Fibers Using Headspace SPME GC/MS at Room Temperature

| analyte | linear range ($\mu g\ L^{-1}$) | slope ± SD[a] | LOD ($\mu g\ L^{-1}$) | R | % RSD[b] | linear range ($\mu g\ L^{-1}$) | slope ± SD | LOD ($\mu g\ L^{-1}$) | R | % RSD |
|---|---|---|---|---|---|---|---|---|---|---|
| | Fiber 4 | | | | | Fiber 6 | | | | |
| ethyl valerate | 1-500 | 24110 ± 363 | 0.5 | 0.999 | 5.9 | 1-500 | 19770 ± 270 | 0.5 | 0.999 | 6.3 |
| 2-methyl-1-butanol | 5-500 | 3483 ± 83 | 2.5 | 0.999 | 5.3 | 5-500 | 2536 ± 16 | 2.5 | 0.999 | 4.5 |
| ethyl hexanoate | 0.1-500 | 103500 ± 1260 | 0.01 | 0.999 | 5.6 | 0.5-500 | 80140 ± 1270 | 0.1 | 0.999 | 8.4 |
| cyclohexanol | 5-500 | 5177 ± 52 | 2.5 | 0.999 | 4.0 | 1-500 | 4782 ± 63 | 0.5 | 0.999 | 5.0 |
| furfural | 1-500 | 3126 ± 22 | 0.5 | 0.999 | 7.0 | 0.5-500 | 2359 ± 19 | 0.1 | 0.999 | 5.3 |
| benzaldehyde | 0.5-500 | 8705 ± 52 | 0.1 | 0.999 | 3.4 | 0.5-500 | 6225 ± 59 | 0.1 | 0.999 | 2.1 |
| 1-octanol | 0.1-500 | 423600 ± 2870 | 0.01 | 0.999 | 3.5 | 0.1-500 | 265000 ± 2000 | 0.01 | 0.999 | 6.7 |
| furfuryl propionate | 0.5-500 | 54750 ± 218 | 0.1 | 0.999 | 5.5 | 1-500 | 36870 ± 164 | 0.5 | 0.999 | 4.1 |
| furfuryl pentanoate | 0.1-500 | 662900 ± 3520 | 0.01 | 0.999 | 2.8 | 0.1-500 | 400000 ± 1870 | 0.01 | 0.999 | 4.8 |
| α-ethyl benzenemethanol | 0.1-500 | 131200 ± 692 | 0.01 | 0.999 | 1.0 | 0.5-500 | 100000 ± 212 | 0.1 | 0.999 | 5.6 |
| | Fiber 10 | | | | | Fiber 12 | | | | |
| ethyl valerate | 0.1-500 | 73570 ± 1460 | 0.01 | 0.998 | 5.5 | 0.5-500 | 69340 ± 1300 | 0.1 | 0.999 | 6.1 |
| 2-methyl-1-butanol | 5-500 | 4617 ± 87 | 2.5 | 0.999 | 7.0 | 1-500 | 9825 ± 84 | 0.5 | 0.999 | 2.9 |
| ethyl hexanoate | 0.1-500 | 199600 ± 3680 | 0.01 | 0.998 | 0.7 | 0.1-500 | 316800 ± 7080 | 0.01 | 0.998 | 8.1 |
| cyclohexanol | 0.1-500 | 8381 ± 178 | 0.01 | 0.998 | 7.4 | 0.1-500 | 14650 ± 289 | 0.01 | 0.999 | 10.0 |
| furfural | 1-500 | 4030 ± 24 | 0.5 | 0.999 | 7.1 | 0.5-500 | 6170 ± 58 | 0.1 | 0.999 | 5.1 |
| benzaldehyde | 0.5-500 | 11990 ± 156 | 0.1 | 0.999 | 0.6 | 0.5-500 | 22030 ± 286 | 0.1 | 0.999 | 4.5 |
| 1-octanol | 0.1-500 | 684400 ± 6880 | 0.01 | 0.999 | 6.7 | 0.1-500 | 1050000 ± 16600 | 0.01 | 0.999 | 4.8 |
| furfuryl propionate | 0.5-500 | 87670 ± 759 | 0.1 | 0.999 | 5.4 | 1-500 | 133500 ± 496 | 0.5 | 0.999 | 2.8 |
| furfuryl pentanoate | 0.1-500 | 951600 ± 8720 | 0.01 | 0.999 | 10.5 | 0.1-500 | 1399000 ± 26200 | 0.01 | 0.998 | 5.6 |
| α-ethyl benzenemethanol | 0.1-500 | 211100 ± 1760 | 0.01 | 0.999 | 4.5 | 0.1-500 | 328900 ± 2860 | 0.01 | 0.999 | 5.5 |

[a]SD: Error of the slope for n = 7.
[b]Determined by performing repeated experiments at 50 $\mu g\ L^{-1}$ (n = 3) using an extraction time of 45 min.

When comparing the sensitivity of the [(VIM)$_2$C$_8$] 2[Br] cross-linked coatings, Fiber 4, which consists of 30% (w/w) cross-linker, exhibited higher slopes for all analytes compared to the higher cross-linked Fiber 6. This observation is especially true for 1-octanol, furfuryl pentanoate, and ethyl hexanoate. The LODs of both fibers ranged from 0.01 to 2.5 $\mu g\ L^{-1}$. The precision, determined by performing triplicate extractions at 50 $\mu g\ L^{-1}$, ranged from 1.0 to 7.0% and 2.1 to 8.4% for Fiber 4 and Fiber 6, respectively. In the case of the two PIL-based coatings containing the [(VIM)$_2$C$_{12}$] 2[Br] IL cross-linker, an increase in the extent of cross-linking (from 30% to 50% w/w cross-linker) resulted in an increase in sensitivity for all analytes. The LOD of many analytes using Fiber 12, containing 50% (w/w) cross-linker, were lower than or equal to those of Fiber 10, except for furfuryl propionate. The LODs ranged from 0.01 to 2.5 $\mu g\ L^{-1}$ and 0.01 to 0.5 $\mu g\ L^{-1}$ for Fiber 10 and Fiber 12, respectively.

Calibration studies were also performed using Fiber AIBN and UV in order to study the effects of linear (i.e., noncross-linked) coatings on sensitivity and precision. Fiber AIBN exhibited higher sensitivity for all studied analytes in comparison to Fiber UV. The LOD of Fiber UV was observed to be lower for some analytes due to higher sorbent coating bleed for Fiber AIBN. This resulted in an elevated background and a higher detection limit. The overall LODs ranged from 0.01 to 2.5 $\mu g\ L^{-1}$ for both fibers with precision ranging from 2.1 to 13.3% and 1.1 to 12.0% for Fibers AIBN and UV, respectively.

Fibers 10 and 12, which contained the more hydrophobic [(VIM)$_2$C$_{12}$] 2[Br] cross-linker, were selected to explore the feasibility of the cross-linked PIL sorbent coatings. Polar analytes possessing low volatility were chosen as targets to examine sorbent coatings for direct immersion SPME in aqueous solutions, which requires coatings that exhibit significantly low solubility in water. Calibration curves were obtained by decreasing analyte concentrations from 75 to 0.01 $\mu g\ L^{-1}$ while using a minimum of seven calibration levels. Direct immersion extractions were performed in deionized water at room temperature with an extraction time of 45 min under agitation. Table 3 below lists the figures of merit for the extraction of these analytes using the two coatings:

TABLE 3

Figures of Merit of Selected Fibers Using Direct Immersion SPME GC/MS at Room Temperature

| analyte | linear range ($\mu g\ L^{-1}$) | slope ± SD[a] | LOD ($\mu g\ L^{-1}$) | R | % RSD[b] | linear range ($\mu g\ L^{-1}$) | slope ± SD | LOD ($\mu g\ L^{-1}$) | R | % RSD |
|---|---|---|---|---|---|---|---|---|---|---|
| | Fiber 10 | | | | | Fiber 12 | | | | |
| 1-octanol | 0.1-75 | 22650 ± 687 | 0.01 | 0.998 | 6.7 | 1-75 | 36240 ± 831 | 0.5 | 0.999 | 6.1 |
| furfuryl pentanoate | 0.5-75 | 32980 ± 1260 | 0.1 | 0.997 | 2.9 | 1-75 | 43280 ± 1370 | 0.5 | 0.999 | 9.4 |
| naphthalene | 0.01-75 | 377900 ± 14400 | 0.001 | 0.996 | 3.2 | 0.01-75 | 453700 ± 4750 | 0.001 | 0.999 | 8.0 |

TABLE 3-continued

Figures of Merit of Selected Fibers Using Direct Immersion SPME GC/MS at Room Temperature

| analyte | linear range (µg L$^{-1}$) | slope ± SD[a] | LOD (µg L$^{-1}$) | R | % RSD[b] | linear range (µg L$^{-1}$) | slope ± SD | LOD (µg L$^{-1}$) | R | % RSD |
|---|---|---|---|---|---|---|---|---|---|---|
| α-ethyl benzenemethanol | 0.01-75 | 8989 ± 294 | 0.001 | 0.997 | 5.9 | 1-75 | 19340 ± 380 | 0.5 | 0.999 | 4.4 |
| phenol | 0.01-75 | 17410 ± 409 | 0.001 | 0.998 | 7.9 | 0.01-75 | 41860 ± 679 | 0.001 | 0.999 | 3.1 |

[a]SD: Error of the slope for n = 7.
[b]Determined by performing repeated experiments at 750 µg L$^{-1}$ (n = 3) using an extraction time of 45 min.

The precision of both fibers remained acceptable, even after multiple extraction and desorption steps, ranging from 2.9 to 6.7% and 3.1 to 9.4% for Fibers 10 and 12, respectively. The sensitivity of all analytes was greater for Fiber 12 compared to its lower cross-linked counterpart. The LODs ranged from 0.001 to 0.1 µg L$^{-1}$ and 0.001 to 0.5 µg L$^{-1}$ for Fibers 10 and 12, respectively.

The performance of Fiber AIBN and Fiber UV (employing no cross-linkers) was also compared. In the case of Fiber AIBN, the coating dissolved almost immediately after being immersed into the sample solution. Therefore, Fiber AIBN is not suitable for direct immersion SPME. However, Fiber UV remained visibly intact within the matrix.

Recovery experiments were performed to evaluate the applicability of the cross-linked PIL sorbent coatings. The experiments were performed by spiking 5 µg L$^{-1}$ into the selected water matrix and exposing the coating to the sample solution for 45 min under agitation. Blank extractions of the sample matrices were performed to ensure no analyte was present prior to analysis. Fibers 6 and 12 were selected as representative coatings for headspace recovery experiments. The percent relative recoveries using deionized water containing 30% (w/v) NaCl ranged from 78.1±6.4% to 119.1±12.6% and 87.8±3.5% to 119.0±12.1% for Fibers 6 and 12, respectively. Fiber 12 was subjected to further examination using more complex sample solutions. Recoveries ranging from 66.3±10.7% to 109.6±4.2% and 74.1±3.2% to 164.7±8.0% were obtained when examining well and river water, respectively.

To further demonstrate the usefulness of the cross-linked PIL coatings synthesized in this example from the methods described herein, Fiber 12 was selected for analysis of select analytes from deionized, well, and river water. The experiments were performed by spiking 2.5 µg L$^{-1}$ of analyte into the water sample and immersing the coating into the sample solution for 45 min under agitation. As seen in Table 4 below, the relative recoveries ranged from 88.9±2.0 to 112.5±10.3% for deionized water. The relative recoveries for well and river water ranged from 58.0±4.1 to 116.0±11.2% and 70.9±3.2 to 135.8±13.8%, respectively. The sorbent coating was capable of withstanding the complex matrix environment to extract analytes at trace-level concentrations, further demonstrating the durability and stability of the cross-linked PIL-based sorbent coatings for direct immersion studies.

All fibers synthesized in this example were sacrificed for analysis via SEM to analyze the coating morphology and determine the appropriate film thickness. SEM images of a representative group of the coatings are shown in FIGS. 6-13. Even after multiple extraction and desorption steps, the coatings used for headspace analysis remained smooth and intact. For the coatings applied in direct studies, a rougher surface morphology was observed. The rigid surface was highly pronounced for Fiber 12, which was immersed into all three water samples for a total of approximately 90 extraction and desorption steps. Without wishing to be bound by theory, it is likely that particulate matter within the complex sample matrix may have affected the morphology of the fiber, particularly true since the only sample preparation performed on the river water sample was to filter particulate matter through a syringe filter. Nevertheless, no discernible loss in analyte extraction efficiency or precision was observed for the fiber coating up until the time it was sacrificed for SEM imaging.

Compared to linear PIL-based sorbent coatings prepared using AIBN-initiated polymerization, many of the cross-linked PIL-based coatings synthesized with UV in this example exhibited lower bleed, lower backgrounds, and lower limits of detection.

EXAMPLE 2

Naphthalene and 1-octanol were purchased from Sigma-Aldrich (Milwaukee, Wis.). 1-vinylimidazole, 1,8-dibromooctane, 1,12-dibromododecane, vinyltrimethoxysilane (VTMS), 2,2'-azobis(2-methylpropionitrile) (AIBN), 1-chlorohexane, ammonium hydrogen difluoride, and 2-hydroxy-2-methylpropiophenone (DAROCUR 1173) were purchased from Sigma-Aldrich. Lithium bis[(trifluoromethyl) sulfonyl]imide (LiNTf$_2$) was purchased from SynQuest Labs (Alachua, Fla.). Acetone and isopropanol were purchased from Fisher Scientific (Fair Lawn, N.J.). Deionized water (18.2 MΩ/cm) was obtained from a Milli-Q water purification system (Millipore, Bedford, Mass.) and was used for the preparation of all aqueous solutions.

Individual standards containing naphthalene and 1-octanol were prepared by dissolving each analyte in acetonitrile at a concentration of 40 mg mL$^{-1}$. Standard stock solutions were prepared by combining the two individual standards at various concentrations and further diluting with acetonitrile. Working solutions were prepared by spiking 75 µL of a standard stock solution into 15 mL of deionized water to yield the desired concentration. The volume of organic modifier in the solution was kept at 0.5% of the entire sample volume.

Separations were performed using an Agilent 7890 gas chromatograph (Santa Clara, Calif.) coupled to a 5975C inert XL MSD with a Triple Axis detector (GC/MS). Detection of naphthalene and 1-octanol were performed using single ion monitoring (SIM) mode wherein ion fragments 102 and 128 were chosen for naphthalene and ion fragments 56, 70, and 84 were chosen for 1-octanol. Helium was used as a carrier gas with a flow rate of 1 mL per min. All separations and analyses were performed in the splitless injection mode using a CP-Wax 57-CB (50 m×250 µm×0.20 µm) column purchased from Agilent Technologies (Palo Alto, Calif.). The following temperature was set to 70° C. and held for 6 min followed by a ramp of 20° C./min to 150° C. The temperature was then increased to 225° C. at a ramp of 10° C./min and held for 10 min.

Homemade SPME fibers were prepared according to the procedures described in Example 1 above. Table 4 below lists the sorbent coating names, structures, and composition, as well as the method employed in polymerization and loading of the sorbent material on the fiber.

promote copolymerization. The derivatized fiber was then dip-coated with the IL monomer(s) and exposed to UV-radiation for 30 min. Subsequently, the PIL-coated fiber was conditioned five times in the GC injector at 175° C. for 5 min.

TABLE 4

| Name | Chemical Structure of Polymer and Crosslinker | Percentage of Cross-linker (% w/w) | Initiator Percentage (% w/w) and Initiator Type | Loading/ polymerization Method |
|---|---|---|---|---|
| PDMS/DVB | 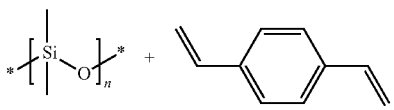 | — | — | — |
| PA | 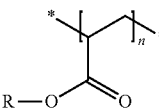 | — | — | — |
| Fiber PIL 1 | 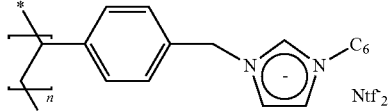 | — | 2% AIBN | Dip-coated; thermal-initiated polymerization |
| Fiber PIL 2 | 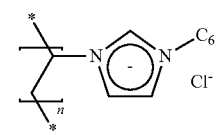 | — | 3% DAROCUR 1173 | On-fiber UV-initiated polymerization |
| Fiber PIL 3 | 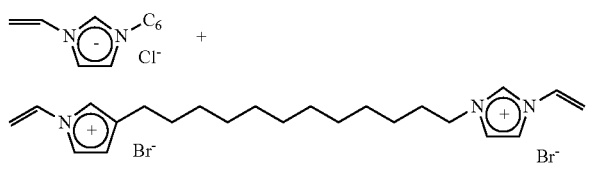 | 50% | 3% DAROCUR 1173 | On-fiber UV-initiated polymerization |
| Fiber PIL 4 | 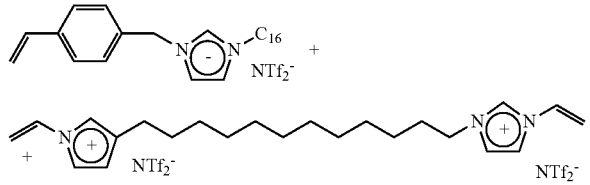 | 50% | 3% DAROCUR 1173 | On-fiber UV-initiated polymerization |

(—) Not applicable or value is unknown

The AIBN-initiated poly([VBHDIM][NTf$_2$]) PIL-based fiber (Fiber PIL 1) was fabricated according to the procedure described in Example 1 above, except an etched bare silica support was used to enhance the overall mechanical stability of the coated fiber. Fiber surface derivatization using a VTMS solution was employed for UV-initiated PIL-based coatings, namely, poly (1-vinyl-3hexylimidazolium) chloride (poly([VHIM][Cl])) (Fiber PIL 2), poly [1,12-di(3-vinylimidazolium)dodecane] dibromide(poly{[(VIM)$_2$C$_{12}$]} 2[Br] in poly([VHIM][Cl] (Fiber PIL 3), and poly[1,12-di (3-vinylimidazolium)dodecane] di{bis[(trifluoromethyl)sulfonyl]imide} (polu{[VIM)$_2$C$_{12}$]} 2[NTf$_2$] in poly(1-4-vinylbenzyl)-3-hexadecylimidazolium bis[(trifluoromethyl) sulfonyl]imide(poly([VBHDIM][NTf$_2$])) (Fiber PIL 4), to incorporate a vinyl substituent on the fiber surface and The coatings synthesized through AIBN-initiated polymerization are linear polymers, whereas the coatings synthesized through the UV-initiated polymerization are cross-linked copolymeric coatings.

SPME experiments were performed at room temperature by exposing a coated fiber to the headspace of a 20 mL amber glass sampling vial (Supelco) containing a specific concentration of 1-octanol and naphthalene. Agitation of the sample solution was achieved by stirring the solution at 750 RPM via a magnetic stir bar. The extraction time was adjusted for equilibration of both analytes. Following extraction, the analytes were desorbed in the GC injector at 175° C. for 5 min. Analyte carryover was monitored for all fibers and was found to be <5%.

Equilibrium was established at 60 min for the PDMS/ DVB coating. However, 1-octanol and naphthalene reached equilibrium with the PA coating in approximately 100 min. Without wishing to be bound by theory, it is believed the large differences in extraction equilibrium times are a function of the dissimilarity in mass transfer between the two coatings. With the exception of Fiber 4, the PIL-based coatings reached equilibrium with both analytes in 60 min. Although the equilibrium sorption time for these coatings is quicker than that of the PA coating, the film thicknesses of these coatings are considerably smaller (approximately 6-10 times). Subsequent to optimization, an extraction time of 60 min was applied for the PDMS/DVB coating along with PIL-based Fibers 1-3. Optimized extraction times of 100 min and 120 min were chosen for the PA coating and Fiber PIL 4, respectively.

To determine whether competition influences the extraction mechanism for the sorbent coatings studied, calibration curves of 1-octanol with concentrations ranging from 1 to 1000 µg L$^{-1}$ were obtained. Naphthalene was also added into the same solution at two relative concentration (µg L$^{-1}$) ratios, namely 10:1 and 1:1 (1-octanol:naphthalene). Tabulated data comparing the sensitivity, defined by the slope of the calibration curve, linear range, variance, and precision of all coatings for the extraction of 1-octanol in the presence of naphthalene are shown in FIGS. 15A-F. For PDMS-DVB, there was a decrease of about 30% on the slope of the analytical curve when the relative concentration of interferent naphthalene is increased ten times. For PA, there is no significant change in the slope of the curve when more interferent is added. The same is seen with PIL Fibers 1 to 4.

Figure 16A:
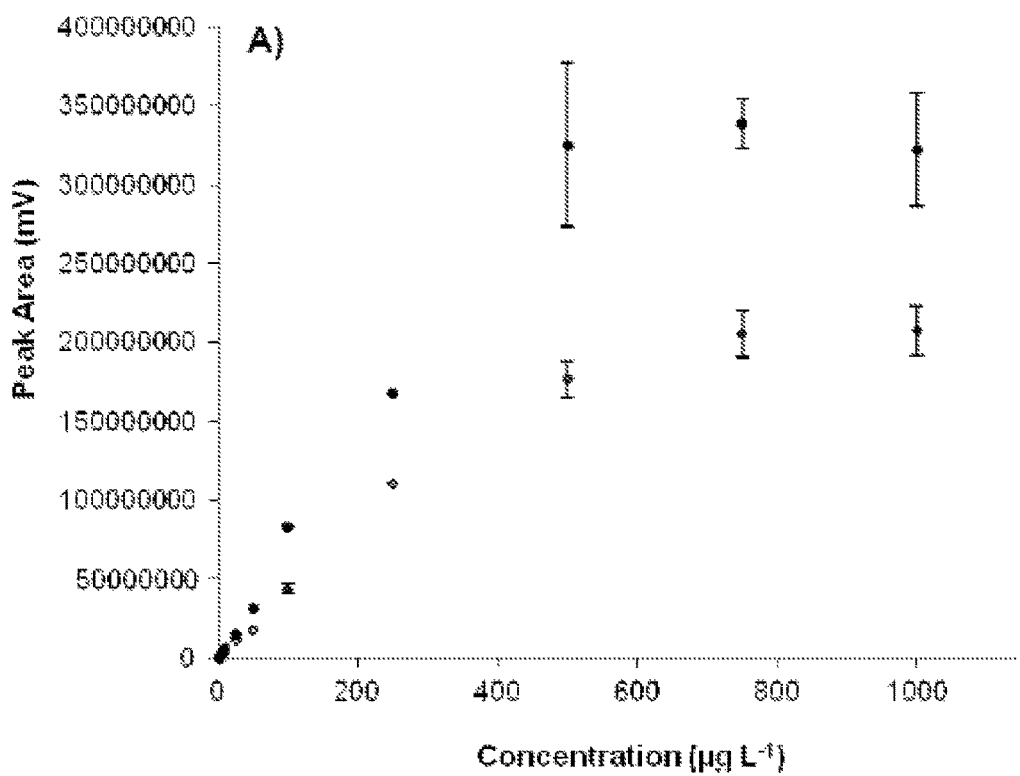
FIGS. 16A-B: Calibration curves for 1-octanol using (A) the PDMS/DVB coating, and (B) the PA coating.
Figure 16B:
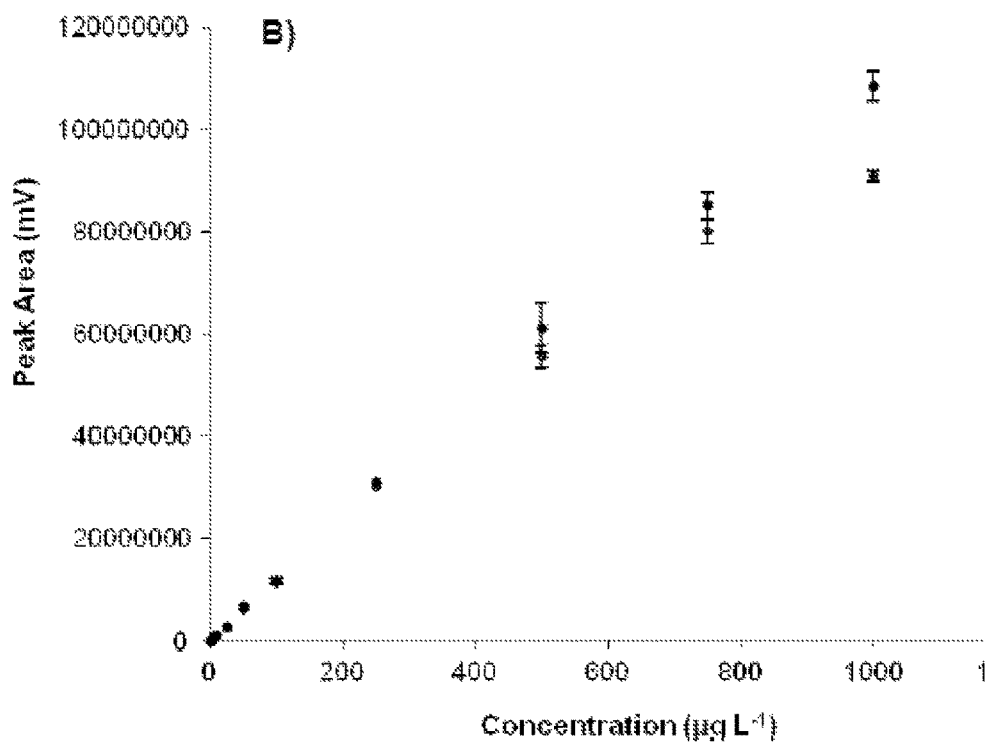

The calibration curves for 1-octanol using the PDMS/DVB coating are shown in FIG. 16. The linear range of 1-octanol at a 10:1 (1-octanol:naphthalene) ratio ranged from 1 to 500 µg L$^{-1}$. When increasing the relative ratio of naphthalene to 1:1 (1-octanol:naphthalene), the upper limit of the linear range decreased to approximately 250 µg L$^{-1}$. The amount of 1-octanol extracted at every concentration studied is significantly lower than the 10:1 (1-octanol:naphthalene) ratio. Additionally, the sensitivity of 1-octanol was significantly reduced. The results indicate the competitive nature of the extraction system, wherein analytes are predominantly adsorbed to the surface of the PDMS/DVB coating. As seen in FIG. 16B, a linear curve for 1-octanol was obtained when using the PA coating at a 10:1 (1-octanol:naphthalene) ratio. When increasing the amount of naphthalene in the sample solution to a 1:1 (1-octanol:naphthalene) ratio, the linear range and sensitivity was largely unaffected. The amount of 1-octanol extracted remained similar up to 750 µg L$^{-1}$. This indicates the lack of analyte competition for the PA coating, which fits a partitioning mechanism. A slight decrease in the upper limit of the linear range from 1000 µg L$^{-1}$ to about 750 µg L$^{-1}$ was also observed, consistent with predominant sorptive behavior for both coatings.

Figure 17A:
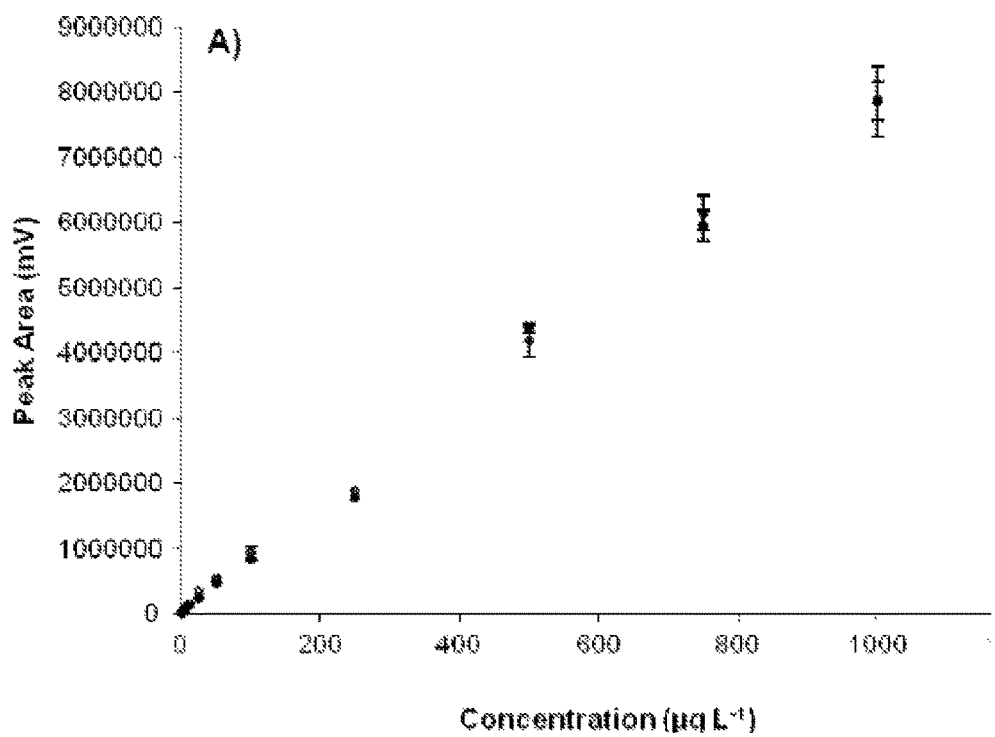
FIGS. 17A-B: Calibration curves for 1-octanol using (A) Fiber PIL 1, and (B) Fiber PIL 2.
Figure 17B:
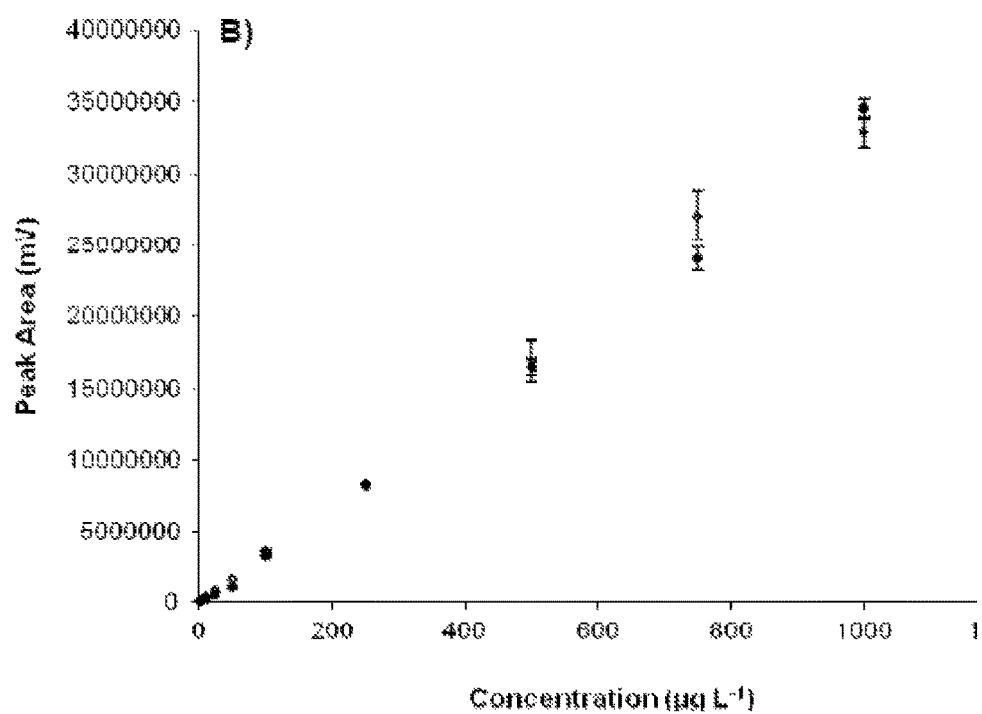

The same competitive inhibition studies were performed for the PIL-based coatings in order to gain insight into their extraction mechanism. The calibration curves plotted for 1-octanol using Fiber PIL 1 is shown in FIG. 17A. The linear range of the calibration curve remained constant from 1 µg L$^{-1}$ to 1000 µg L$^{-1}$ when naphthalene was present at both low and high relative ratios. Additionally, the sensitivity and amount of 1-octanol extracted remained unaffected. This indicates little to no competition between the two chosen analytes, which is characteristic of a partitioning mechanism. Fiber PIL 2 was studied to investigate the effect of UV-initiated on-fiber polymerization. The results shown in FIG. 17B for Fiber PIL 2 are similar to Fiber PIL 1 and the PA coating; only negligible changes in the linear range, sensitivity, and amount of 1-octanol extracted were observed.

Figure 18A:
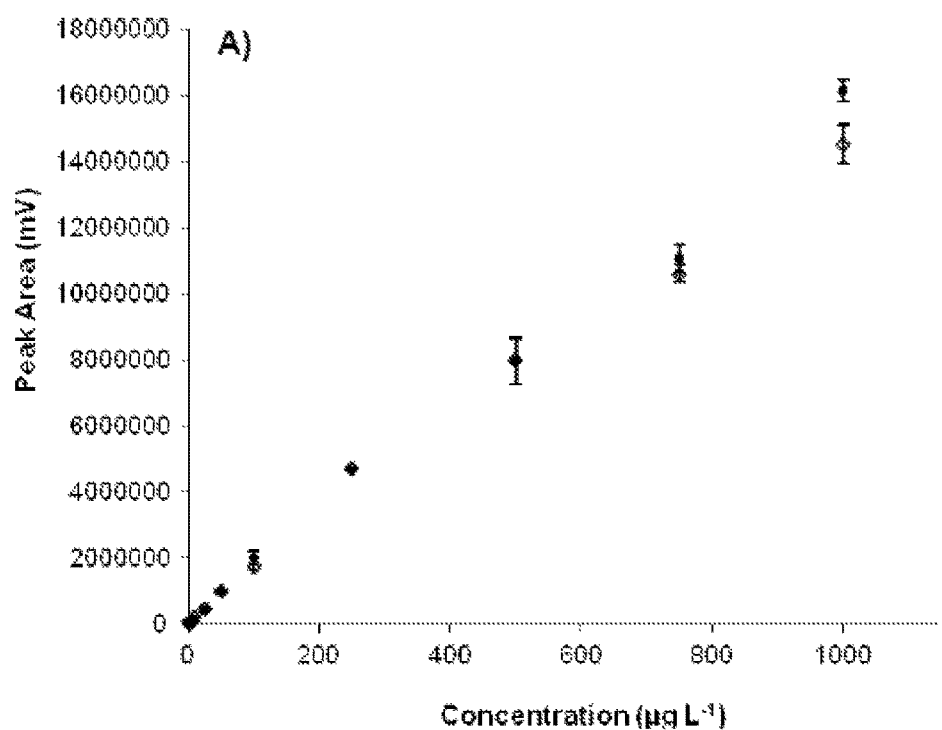
FIGS. 18A-B: Curves showing the linear range, sensitivity, and amount of 1-octanol extracted using (A) Fiber PIL 3, and (B) Fiber PIL 4.
Figure 18B:
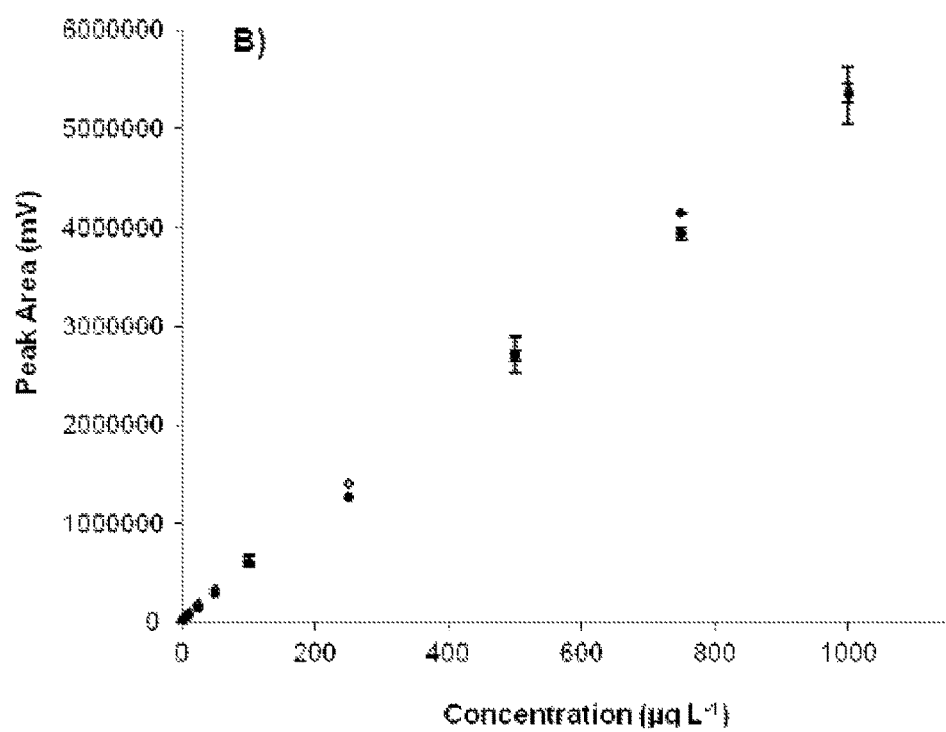

The extraction mechanism of the two crosslinked PIL-based coatings, namely PIL Fibers 3 and 4, containing the same IL monocationic monomers used in PIL Fibers 1 and 2, was explored. These coatings were synthesized using a high percentage of dicationic IL crosslinker (50% w/w of crosslinker to monomer) and were observed to be more rigid than their non-crosslinked counterparts. As shown in FIGS. 18A-B, the linear range, sensitivity, and amount of 1-octanol extracted are similar using both crosslinked PIL-based coatings. The results indicate that the rigid PIL-based copolymeric sorbent coatings also exhibit similar partitioning behavior to their non-crosslinked counterparts.

While the invention has been described with reference to various and preferred embodiments, it should be understood by those skilled in the art that various changes may be made and equivalents may be substituted for elements thereof without departing from the essential scope of the invention. In addition, many modifications may be made to adapt a particular situation or material to the teachings of the invention without departing from the essential scope thereof.

Therefore, it is intended that the invention not be limited to the particular embodiment disclosed herein contemplated for carrying out this invention, but that the invention will include all embodiments falling within the scope of the claims.

What is claimed is:

1. A method of making a photo-initiated polymeric ionic liquid (P-PIL) coated support, comprising:
   i) mixing at least one ionic liquid (IL) monomer with at least one photo-initiator;
   ii) at least partially coating a support with the mixture of step i), wherein the support is a fiber; and
   iii) exposing the coated support of step ii) to UV light to form a photo-initiated polymeric ionic liquid (P-PIL) coated support;
   wherein at least a portion of a surface of the support is functionalized by etching with a vinyl substituent prior to coating with the IL monomer mixture.

2. The method of claim 1, further including adding at least one cross-linker to the mixture of step i).

3. The method of claim 1, wherein about 2% to about 4% (m/v) of photo-initiator is added to the mixture.

4. The method of claim 1, wherein the coated support of step ii) is exposed to UV light in the range of about 250-240 nm.

5. The method of claim 1, wherein the coated support of step ii) is exposed to UV light for a time period of about 2 hours.

6. The method of claim 1, wherein the P-PIL is synthesized by a polymerization reaction involving one or more functional groups attached to an aromatic ring of a cationic component.

7. The method of claim 1, wherein the photo-initiator comprises 2-hydroxy-2-methylpropiophenone (HMPP).

8. The method of claim 1, wherein the degree of crosslinking is modified to control the consistency of the formed polymer with greater degrees of crosslinking resulting in a more rigid coating.

9. The method of claim 1, wherein the P-PIL is synthesized using a cross-linking reaction.

10. The method of claim 9, wherein the degree of crosslinking is modified to influence either the mechanism of portioning or the overall selectivity for targeted analyte molecules.

11. The method of claim 1, wherein the photo-initiated polymeric ionic liquid (P-PIL) comprises:
- at least one cationic component comprising an ionic liquid (IL), and
- one or more anionic components, wherein the anionic components can be the same or different.

12. The method of claim 1, wherein the photo-initiated polymeric ionic liquid (P-PIL) is a c-P-PIL comprising:
- at least one ionic liquid comprising an anionic component, and
- one or more mobile cationic components, wherein the cationic components can be the same or different.

13. The method of claim 11, wherein the cationic component comprises one or more imidazolium-based monomers selected from the group consisting of functionalized imidazolium, pyridinium, phosphonium, triazolium, pyrrolidinium, and ammonium.

14. A P-PIL coated support made by the method of claim 1, wherein the photo-initiated polymeric ionic liquid (P-PIL) comprises:
- at least one cationic component comprising an ionic liquid (IL), and
- one or more anionic components, wherein the anionic components can be the same or different.

15. The P-PIL coated support of claim 14, wherein the cationic component comprises at least one or more of: quaternary ammonium, protonated tertiary amine, thionium, phosphonium, arsonium, carboxylate, sulfate or sulfonate groups which may be substituted or unsubstituted, saturated or unsaturated, linear, branched, cyclic or aromatic.

16. The P-PIL coated support of claim 14, which is polymerized to form linear polymers and/or cross-linked polymers, using varying ratios of monocationic/dicationic/tricationic/multicationic crosslinking molecules.

* * * * *